United States Patent [19]

Brock et al.

[11] Patent Number: 5,330,682

[45] Date of Patent: Jul. 19, 1994

[54] METHODS OF EMULSIFICATION WITH PEPTIDE EMULSIFIERS

[75] Inventors: Christopher J. Brock, Wallingford, United Kingdom; Michael B. Enser, Winscombe, England

[73] Assignee: Agricultural & Food Research Council, Berkshire, England

[21] Appl. No.: 488,016

[22] PCT Filed: Nov. 3, 1988

[86] PCT No.: PCT/GB88/00969

§ 371 Date: May 4, 1990

§ 102(e) Date: May 4, 1990

[87] PCT Pub. No.: WO89/04209

PCT Pub. Date: May 18, 1989

[30] Foreign Application Priority Data

Nov. 7, 1987 [GB] United Kingdom ............... 8726132
Jul. 1, 1988 [GB] United Kingdom ............... 8815748

[51] Int. Cl.$^5$ .................... B01J 13/00; B01F 17/30
[52] U.S. Cl. .................................... 252/314; 252/308; 252/312; 252/356; 426/602
[58] Field of Search ............... 252/308, 312, 356, 357, 252/314; 426/602; 530/328

[56] References Cited

U.S. PATENT DOCUMENTS

4,943,527 7/1990 Protter et al. ................ 435/69.6
5,135,736 8/1992 Anderson et al. ............. 424/1.1

FOREIGN PATENT DOCUMENTS

0160103 11/1985 European Pat. Off. .
WO89/06657 7/1989 World Int. Prop. Q. .......... 530/326

OTHER PUBLICATIONS

P. Dunnill, Biophysical J. 8:865–875 (1968).
E. T. Kaiser and F. J. Kezdy, Science 223:249–255 (1984).
Stephen J. Kennedy, J. Memb. Biol. 42:265–279 (1978).
Kevin N. Pearce and John E. Kinsella, J. Agric. Food Chem. 26:716–723 (1978).
Stephen W. Provencher and Jurgen Glockner, Biochemistry 20:33–37 (1981).
Stephen W. Provencher, Computer Physics Communications 27:229–242 (1982).
E. Kaiser et al., Short Communication Anal. Biochem. 34: 595–598 (1970).
Harpers Review of Biochemistry, 20th Ed. p. 35.
J. T. Sparrow et al., Proc. Amer. Peptide Symp. Proc. 9, Peptides and Function, 1987, pp. 865–874.
Chem. Abstracts vol. 167, 1987 E. Dickinson Abst. No. 31418d.
R. M. Epand et al. Proc. Amer. Peptide Symp., Proc. 9, Peptides Structue and Function 1987, pp. 875–878.
Segrest et al., "A Theory of Lipid-Protein Interactions in the Plasma Lipoproteins", *FEBS Letters*, vol. 38, No. 3, pp. 247–253 (1974).
M. Schiffer et al., "Use of helical wheels to represent the structures of proteins and to identify segments with helical potential," Biophysical Journal, vol. 7, 1967.
E. T. Kaiser et al., "The Design and Construction of Peptides and Proteins with Amphiphilic Secondary Sturctures," Proceedings of The Amer. Peptide Symposium Proc. 9, Peptides Structure and Function, 1987, pp. 855–864.
Chem. Abstract, vol. 106, 1987 E. Dickenson, "Mixed Protein aceous emulsifiers: review of competitive protein absorbtion and the relationship to food colloid stabilization".

*Primary Examiner*—Robert L. Stoll
*Assistant Examiner*—Daniel S. Matzmaier
*Attorney, Agent, or Firm*—Felfe & Lynch

[57] ABSTRACT

Polypeptides which consist substantially of alpha-helix-forming amino acid sequences are useful as emulsifiers, if the helix has at least one hydrophilic axial domain and at least one hydrophobic axial domain such that the helix can adapt a log-in-water orientation at a fat-water interface. The hydrophobic domain may occupy 80°–280° of the circle defined by the helix.

12 Claims, 14 Drawing Sheets

— Polypeptide backbone
---- Potential salt bridge

FIG. 3
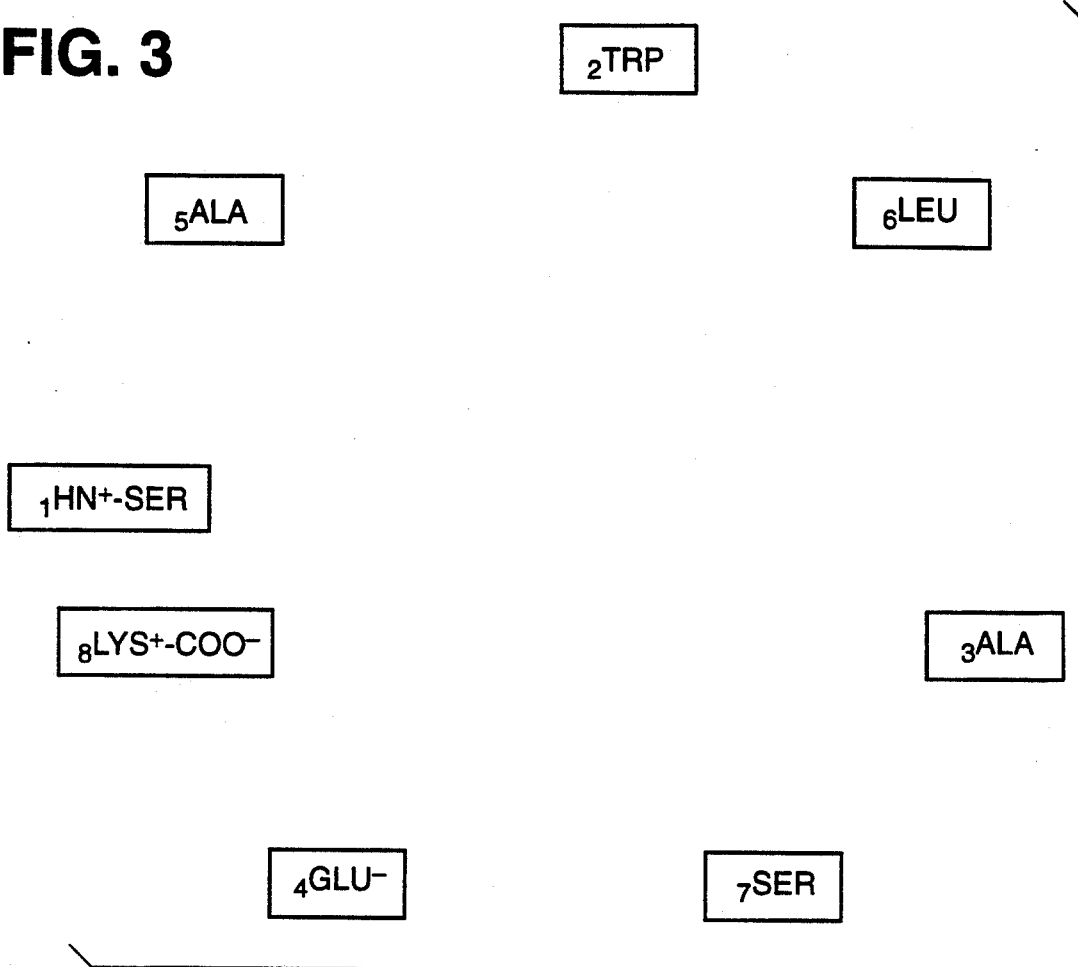
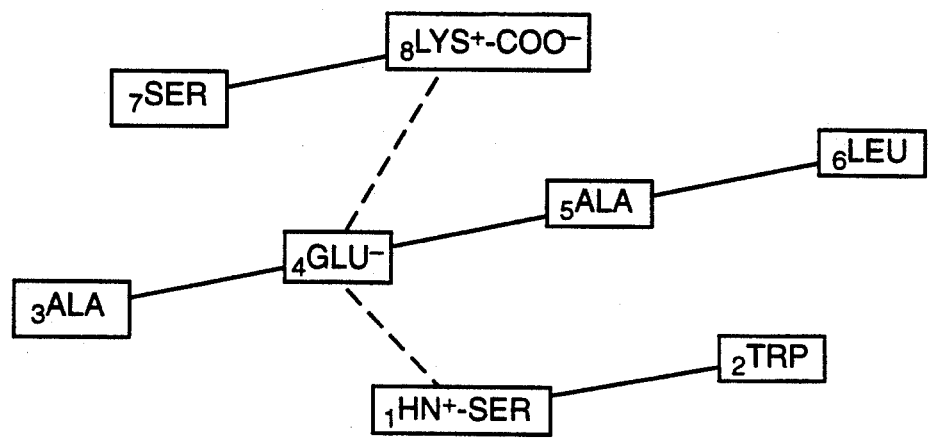
FIG. 4
——— Polypeptide backbone
– – – Potential salt bridge ———— Polypeptide backbone
− − − − − Potential salt bridge — Polypeptide backbone
- - - Potential salt bridge — Polypeptide backbone
--- Potential salt bridge — Polypeptide backbone
- - - - Potential salt bridge ——— Polypeptide backbone
- - - - - Potential salt bridge

METHODS OF EMULSIFICATION WITH PEPTIDE EMULSIFIERS

SUMMARY

This invention concerns the structure and use of peptide emulsifiers in such industrial products as foods, cosmetics, and pharmaceuticals.

BRIEF DESCRIPTION OF THE DRAWINGS

FIGS. 1, 3, 5, 7, 9, 11, 13, 15 and 17 are helical wheel representations of the structure of peptides 1, 2, 3, 4, 5, 6, 7, 8 and 9 respectively.

FIGS. 2, 4, 6, 8, 10, 12, 14, 16, and 18 are helical net representations of the structure of peptides 1, 2, 3, 4, 5, 6, 7, 8 and 9 respectively.

DESCRIPTION OF THE INVENTION

Figure 1:
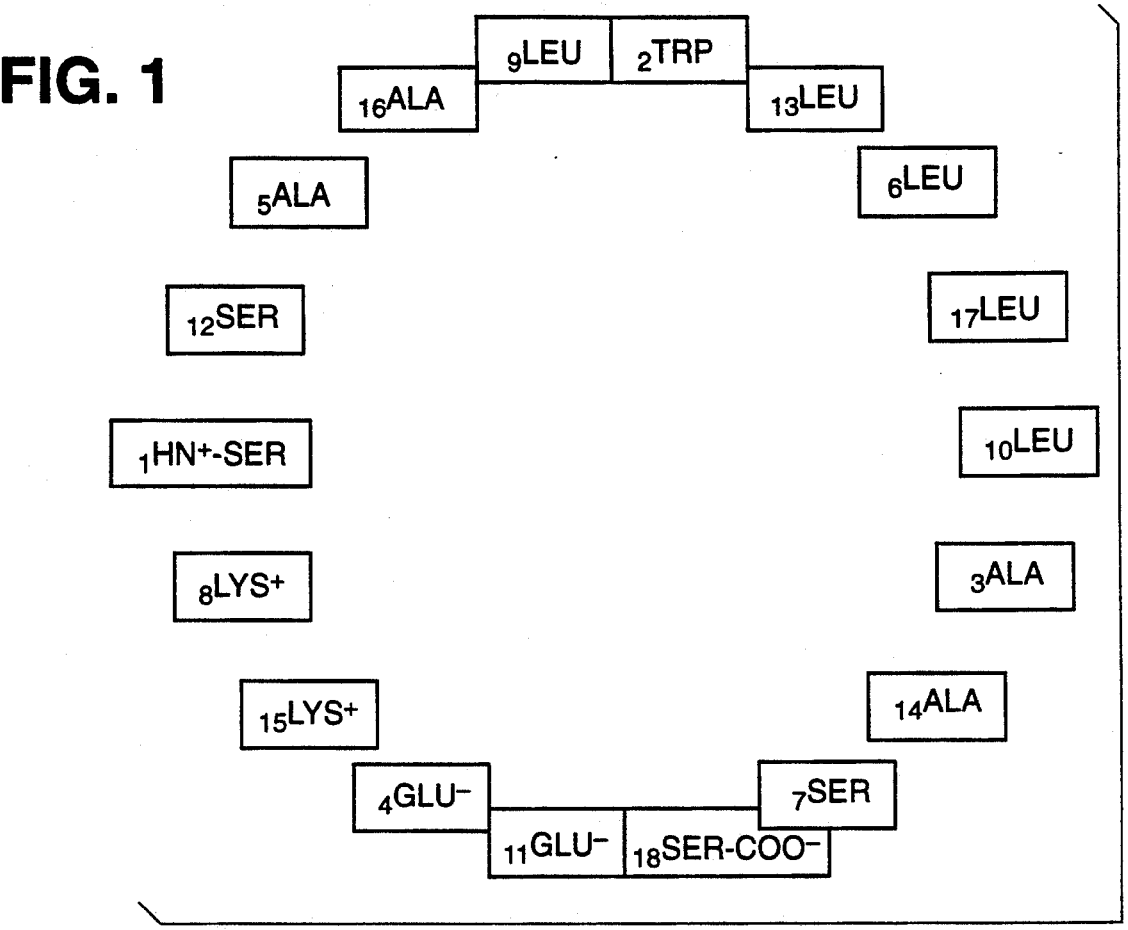

This invention relates to emulsifiers.

Colloids are dispersions of particles of an immiscible substance in a liquid. An emulsion is a dispersion of one immiscible liquid in another, a foam is a dispersion of gas bubbles in a liquid, and a suspension is a dispersion of solid particles in a liquid. Colloids are thermodynamically unstable, because of their high interfacial energy. If a suitable pathway is available to them they will separate into two discrete phases with the minimum possible interfacial area between them. An emulsifier is a substance which acts at the interface between the two phases in a colloid. Such a molecule is amphipathic, which means that separate parts of its structure have affinities for each of the two phases, even though the phases do not have any affinity for each other. Consequently it occupies the interface and lowers the interfacial energy, so that less work has to be done to create a colloidal dispersion from two separate phases than if the emulsifier was absent. An effective emulsifier also forms a film at the interface, the structural integrity of which has to be disrupted for the phases to separate again. Thus, although the colloid remains thermodynamically unstable it is stabilized by kinetic constraints on breakage.

Emulsifiers are frequently used in food preparation. Most such emulsifiers are lipid derivatives such as fatty acid esters. Emulsifiers such as these are excellent at aiding emulsion formation, but do not form strong interfacial films. Consequently they are often used in conjunction with stabilizers, which increase the viscosity of the continuous phase, thus immobilizing the particles which comprise the dispersed phase, and preventing them from coalescing.

Almost all proteins are surface active to some extent, and so they too are used as emulsifiers in food products (see Pearce & Kinsella, J. Agric. Food Chem., 26(3), 716-723, 1978), However, few if any proteins have evolved specifically to become an emulsifier, and only a few proteins have natural functions which are in any way related to emulsification, for example caseins and lipoproteins.

All proteins are surface active to some extent, and this activity can usually be enhanced if they are partially denatured (e.g. by mechanical treatment or heating), so that their amphipathic structural elements are exposed to interact with an interface and with other protein molecules. The possible role of alpha helices, having hydrophilic and hydrophobic faces, in lipid-polar interfaces has been disclosed (see, for example, the respective papers by Kaiser et al, Sparrow et al and Epand et al in "Peptides: Structure and Function", Proc. Am. Peptide symp. 9, 1985) but largely in the case of receptor-ligand interactions. No one has previously proposed using substantially isolated alpha helices as emulsifiers.

One aspect of the present invention provides an emulsifier comprising a polypeptide consisting substantially of at least one region which is capable of forming an alpha-helix having hydrophilic and hydrophobic axial domains such that the said region of the polypeptide may lie on a fat/water interface with the hydrophilic domain in the water phase and the hydrophobic domain in the fat phase, the said alpha-helix having at least 2 turns.

By "consisting substantially" of alpha helix, we mean that the polypeptide has at least a majority of amino acid residues which are of such a nature and which are so arranged that they will tend to form an alpha helix. Clearly, it is not enough that most of the residues should be alpha-helix-forming in themselves, if they alternate with non-helix-forming residues. However, the invention encompasses compounds having more than 70% of its backbone residues capable of forming an alpha helix.

Preferably, at least 80%, 90% or 95% of or all of the backbone residues are capable of forming an alpha helix. Any non-helix-forming residues are preferably located at the ends of the peptide. Thus, in the case of a typical 15-20 amino acid peptide, there are preferably no more than two non-helix-forming residues at each end, more preferably only one at each end and most preferably none at all.

Preferably, the whole polypeptide is capable of lying along the fat/water interface with the hydrophilic domain in the water phase and the hydrophobic domain in the fat phase.

There may be axial domains of intermediate polarity separating the hydrophobic and hydrophilic domains and there may be more than one hydrophobic or hydrophilic domain, but preferably there is Just one hydrophobic domain, one hydrophilic domain and no domains of intermediate polarity. The hydrophobic domain may occupy 80° to 280° (for example 180° or 240° C. of the Circle defined by the helix.

Preferably, the amino acids in the hydrophobic domain contribute to the stabilization of the overall configuration by hydrophobic interactions. This is facilitated if the amino acids have hydrophobic side chains and particularly if they are leucine, alanine or large aromatic groups such as tryptophan which have a high propensity for occurring in alpha-helices. Similarly, it is desirable, although less important, for the hydrophilic amino acids to be so chosen that intra-molecular salt bridges are formed between amino acids which are 3 or 4 residues apart. Suitable amino acids include glutamic acid, lysine and serine.

The use as emulsifiers of known polypeptides which satisfy the criteria given above forms an aspect of the invention.

Such polypeptides have been found to act as emulsifiers. The, alpha-helix may constitute all of the polypeptide, and to optimize functionality this will often be preferred, or there may be additional portions, provided only that such portions do not interfere with the ability of the alpha-helix (or, preferably, the whole molecule) to lie as described on the fat/water interface.

Thus, in addition to any non-helix-forming residues in the backbone of the peptide, the criteria for which are discussed above, there may be helix-forming or non-helix forming amino acids or other groups forming side chains. Such side groups should have the same hydrophilicity as the backbone amino acid to which they are attached. Preferably, the molecular weight of such a side group is less than 200 Daltons, more preferably less than 100 Daltons.

There are preferably at least 11 amino acids in the peptide, suitably no more than 14, and the alpha-helix preferably has at least 4, 5, 6 or 7 turns. It is probable that a very long molecule would be less mobile which could reduce its emulsion-forming activity. However, in general, the longer the molecule the better will be its emulsion-stabilising properties, because all its binding interactions with the interface have to be broken simultaneously for it to leave the interface, and thereby disrupt the interfacial layer of which it is part. A peptide of only 2 or 3 turns does not have the exceptional emulsifying activity of the longer peptides, but is nevertheless similar in activity to proteins used as emulsifiers in foods, and may therefore be useful.

It is to be noted that the extent to which a peptide Forms an alpha-helix depends not only on the sequence of amino acids but also on the environment. For example, trifluoroethanol encourages the formation of alpha-helices, more than a simple 25 mM sodium phosphate solution at pH 7.0. Thus, the terms "alpha-helix" or "capable of forming an alpha-helix" are not absolute but are relative and are used in comparison with other peptides in the same environment.

Nevertheless, there are clear rules, for example those disclosed by Chou and Fasman, for deciding on whether a given amino acid is, in itself, helix-promoting, helix-destabilizing or helix-breathing. The helix-forming amino acids are alanine, leucine, phenylalanine, tyrosine, tryptophan, cysteine, methiomine, histidine, asparagine, glutamine and valine. The helix-destabilizing amino acids are serine, isoleucine, threonine, glutamic acid, aspartic acid, lysine, arginine and glycine. The two helix-breaking amino acids are proline and hydroxyproline. The helix-destabilizing amino acids may nevertheless be present in the peptides of the invention if there are sufficient helix-promoting amino acids for the peptide to be regarded as helix-forming. Thus, it is more accurate to refer to helix-forming sequences than to helix-forming amino acids in isolation. The rules propounded by Chou and Fasman may be used to decide whether a sequence is helix-forming. Alternatively, the location of a given peptide in a Ramachandran plot of the psi angle versus the phi angle can be used to determine whether an "allowable" alpha helix is formed, as is well known to those skilled in this art.

Circular dichroism tests may be used to provide empirical evidence of helix Formation, but this depends very much on the environment to which the compound is exposed. In such a test, a hydrophobic-hydrophilic interface should be used, for example, an aqueous solution of the compound between two glass microscope slides. However, the theoretical criteria discussed above are preferred in determining the character of the compounds.

As is well known in the emulsifiers art, the peptides should be sufficiently soluble in water to allow them to function as emulsifiers. The more hydrophobic compounds of the invention may benefit from having one or more hydrophilic amino acids (helix-forming or non-helix-forming) added to at least one end.

Unless indicated otherwise, the amino acids in the polypeptides of the invention are all in the naturally-occurring L-form. It would be possible also to construct the polypeptide entirely from D-amino acids, but would be considerably more expensive.

The emulsifiers of the invention are harmless when taken orally and indeed have nutritional value; they are therefore ideally suited for use as food emulsifiers, for example in the manufacture of mayonnaise, ice-cream, margarine, spreads, biscuits and a myriad of other modern, processed foodstuffs. They are, however, of more general utility, for example in the manufacture of cosmetics (such as sunscreens and lipsticks), toothpaste and other colloidal systems. Their behaviour in model systems suggests that they will also have utility in novel systems which could be created if a suitable emulsifier existed. Such systems include foams incorporating high levels of lipid (such as canned cream), emulsions which are sensitive to overprocessing, pharmaceutical preparations, cleansing formulations (for example for contact lenses), biosensors and thermodynamically-stable microemulsions.

A second aspect of the invention provides a polypeptide selected from the group consisting of:

(1) $NH_2$-Ser-Trp-Ala-Glu-Ala-Leu-Ser-Lys-Leu-Leu-Glu-Ser-Leu-Ala-Lys-Ala-Leu-Ser-COOH (2) $NH_2$-Ser-Trp-Ala-Glu-Ala-Leu-Ser-Lys-COOH (3) $NH_2$-Ser-Trp-Ala-Glu-Ala-Leu-Ser-Lys-Leu-Leu-Glu-Ser-Leu-Ala-Lys-Ala-Leu-Glu-Ser-Leu-Ala-Lys-Ala-Leu-Glu-Ser-COOH (4) $NH_2$-Ser-Trp-Leu-Glu-Leu-Leu-Leu-Lys-Leu-Leu-Ala-Ala-Leu-Leu-Glu-Leu-Leu-Leu-Lys-Leu-Leu-Ser-COOH (5) $NH_2$-Ser-Trp-Glu-Glu-Glu-Leu-Lys-Lys-Ser-Ser-Glu-Glu-Leu-Lys-Lys-Lys-Leu-Ser-COOH (6) $NH_2$-Ser-Trp-Ala-Glu-Ala-Leu-Ser-Lys-Leu-Leu-Ser-COOH (7) $NH_2$-Ser-Trp-Ala-Glu-Ala-Leu-Ser-Lys-Leu-Leu-Glu-Ser-Leu-Ala-Lys-COOH (8) $NH_2$-Ser-Trp-Ala-Glu-Ala-Leu-Ser-Lys-Leu-Leu-Glu-Ser-Leu-Ala-Lys-Ala-Leu-Glu-Ser-Leu-Ala-Lys-COOH (9) $NH_2$-Ser-Trp-Ala-Glu-Ala-Leu-Ser-Lys-Leu-Leu-Glu-Ser-Leu-Ala-Lys-Ala-Leu-Ser-Glu-Leu-Ala-Lys-Ala-Leu-Ser-Glu-Leu-Leu-Lys-COOH

(10) $NH_2$-Ser-Trp-Ser-Glu-Glu-Leu-Lys-Lys-Ala-Ala-Glu-Glu-Leu-Lys-Lys-Ser-Leu-Ser-COOH

(11) $NH_2$-Ser-Trp-Ala-Glu-Ser-Leu-Lys-Lys-Ala-Ala-Glu-Glu-Leu-Ser-Lys-Ala-Leu-Ser-COOH

(12) $NH_2$-Ser-Trp-Leu-Glu-Ala-Leu-Ala-Lys-Leu-Leu-Ser-Ser-Leu-Ala-Glu-Ala-Leu-Ala-Lys-Leu-Leu-Ser-COOH

(13) $NH_2$-Ser-Trp-Leu-Ala-Ala-Leu-Leu-Glu-Leu-Leu-Leu-Ala-Leu-Leu-Ala-Leu-Leu-Leu-Lys-COOH

(14) $NH_2$-Ser-Trp-Ala-Glu-Ala-Leu-Ser-Arg-Leu-Leu-Glu-Ser-Leu-Ala-Arg-Ala-Leu-Ser-COOH

(15) $NH_2$-Ser-Trp-Ala-Glu-Ala-Leu-Ser-His-Leu-Leu-Glu-Ser-Leu-Ala-His-Ala-Leu-Ser-COOH

(16) $NH_2$-Ser-Trp-Ala-Asp-Ala-Leu-Ser-Lys-Leu-Leu-Asp-Ser-Leu-Ala-Lys-Ala-Leu-Ser-COOH

(17) $NH_2$-Thr-Trp-Ala-Glu-Ala-Leu-Thr-Lys-Leu-Leu-Glu-Thr-Leu-Ala-Lys-Ala-Leu-Thr-COOH

(18) $NH_2$-Gln-Trp-Ala-Glu-Ala-Leu-Gln-Lys-Leu-Leu-Glu-Gln-Leu-Ala-Lys-Ala-Leu-Gln-COOH

(19) NH₂-Asn-Trp-Ala-Glu-Ala-Leu-Asn-Lys-Leu-Leu-Glu-Asn-Leu-Ala-Lys-Ala-Leu-Asn-COOH

(20) NH₂-Met-Trp-Ala-Glu-Ala-Leu-Met-Lys-Leu-Leu-Glu-Met-Leu-Ala-Lys-Ala-Leu-Met-COOH

(21) NH₂-Cys-Trp-Ala-Glu-Ala-Leu-Cys-Lys-Leu-Leu-Glu-Cys-Leu-Ala-Lys-Ala-Leu-Cys-COOH

(22) NH₂-Ser-Trp-Gly-Glu-Gly-Leu-Ser-Lys-Leu-Leu-Glu-Ser-Leu-Gly-Lys-Gly-Leu-Ser-COOH

(23) NH₂-Ser-Trp-Ala-Glu-Ala-Val-Ser-Lys-Val-Val-Glu-Ser-Val-Ala-Lys-Ala-Val-Ser-COOH

(24) NH₂-Ser-Trp-Ala-Glu-Ala-Ile-Ser-Lys-Ile-Ile-Glu-Ser-Ile-Ala-Lys-Ala-Ile-Ser-COOH

(25) NH₂-Ser-Trp-Ala-Glu-Ala-Phe-Ser-Lys-Phe-Phe-Glu-Ser-Phe-Ala-Lys-Ala-Phe-Ser-COOH

(26) NH₂-Ser-Trp-Ala-Glu-Ala-Trp-Ser-Lys-Trp-Trp-Glu-Ser-Trp-Ala-Lys-Ala-Trp-Ser-COOH

(27) NH₂-Thr-Trp-Gly-Asp-Gly-Ile-Thr-Arg-Ile-Ile-Asp-Thr-Ile-Gly-Arg-Gly-Ile-Thr-COOH

(28) NH₂-Tyr-Trp-Tyr-Glu-Tyr-Phe-Tyr-Lys-Phe-Phe-Glu-Tyr-Phe-Tyr-Lys-Tyr-Phe-Tyr-COOH.

and variants thereof wherein (i) Glu is substituted for Gln or vice versa and/or (ii) Asp is substituted for Asn or vice versa and/or (iii) there are up to two non-helix-forming amino acids at each end of the peptide.

The polypeptides may be made by peptide synthesis, for example by the general method of Marglin and Merrifield (Ann.Rev.Biochem., 39, 841–866, 1970) or by the Fmoc-polyamide method of Atherton, Sheppard and their co-workers and by subsequent refinements of these approaches. Alternatively, they may be made biosynthetically in an appropriately transformed host, or by proteolytic degradation of a natural or non-natural protein or polypeptide. It may be particularly advantageous to design a rDNA construct such that a long length of repetitive polypeptide is produced which is then chemically or proteolytically cleaved to give many molecules in accordance with the invention. Chemical cleavage may be by way of cyanogen bromide cleavage, for example of Asp-Asp bonds. Alternatively, if only a short non-helix-forming sequence is provided between each helix-forming sequence, cleavage may be unnecessary. In such a case, the non-helix-forming sequence should be as flexible as possible, so that successive helices can all take up the log-in-water orientation at the fat-water interface.

EXAMPLES

The process of peptide design was carried out on paper with two diagrammatic aids. One was a helical wheel (Schiffer and Edmundson, 1967), which is a two-dimensional representation of an alpha-helix viewed down the length of its axis (e.g. FIG. 1). It illustrates the way in which the amino-acid side chains radiate out from the helix and comprise its cylindrical surface. This enabled the boundaries running parallel to the helix axis between different elements of structure, particularly those of the hydrophobic and hydrophilic surfaces, to be defined. The other representation was a helical net (Dunnill, 1968), which shows the amino acids as though they were projected onto a cylinder wrapped around the helix, which is cut open along a line parallel with the helix axis and laid flat (e.g. FIG. 2). This enabled the interactions between amino acids on adjacent turns of the helix, especially intramolecular salt bridges, to be plotted.

Families of peptides were designed and synthesized in which a single structural feature was varied systematically in order to determine the effect on functionality. By so doing sets of structures were identified which would be potentially useful surface-active agents.

Peptides were obtained for study by semi-automated solid-phase peptide synthesis using a CAR Pepsynthesiser II (Cambridge Research Biochemicals Ltd, Cambridge, U.K.). Peptides were synthesized from active esters (or occasionally symmetrical anhydrides) of 9-fluorenyl-methoxycarbonyl amino acids using the instrument manufacturer's standard procedures. The progress of coupling and deprotection reactions was followed by monitoring the absorbance at 365 nm of the liquid leaving the reaction column. The completion of the coupling reaction was also determined by carrying out the Kaiser test (Kaiser et al, 1970) on a few grains of the solid support, and by observing the disappearance from the reaction column of the yellow colour due to the anionic form of 3,4-dihydro-3-hydroxy-4-oxo-1,2,3-benzotriazine, which was added with the activated amino acid.

The emulsion-forming activities of peptides relative to each other, and to standard proteins, were determined using a variation on the turbidimetric technique of Pearce and Kinsella (1978). Standard emulsification conditions were 5 ml glycerol trioleate and 5 ml 0.2 mg.ml$^{-1}$ peptide or protein in water in a 25 ml Pyrex (Regd. T.M.) glass measuring cylinder, emulsified for 20 s with a Polytron (Kinematica GmbH, Luzern, Switzerland) on speed 5, while cooled on ice. The aqueous phase and the freshly made emulsion were both degassed carefully in vacuo to eliminate any foam. After leaving overnight to allow any non-emulsified oil droplets to coalesce and for the emulsion phase to separate from the residual oil and aqueous phases, the dispersed phase volume fraction in the emulsion was estimated from the levels of the phase interfaces in the measuring cylinder. The contents of the cylinder were mixed gently with a spatula until they were evenly dispersed and immediately a sample was taken and diluted one thousand-fold with water, and with 0.1% sodium dodecyl sulphate (SDS). The optical density at 500 nm of these diluted emulsions was proportional to their turbidity which gave an estimate of the relative emulsion forming activities of the emulsifiers. Higher turbidity in 0.1% SDS than in water indicates that the emulsified particles are aggregated in water. Lower turbidity in 0.1% SDS than in water indicates that the emulsion is destabilize by the added detergent, implying that the emulsion stabilizing activity of the emulsifier is limited.

The conformation of polypeptide emulsifiers in aqueous solution was estimated from far ultra-violet circular dichroism spectra recorded on a Jasco J-B600 spectropolarimeter (Jasco Inc., Easton, Md., USA). Spectra were recorded from peptide solutions of 0.1 to 1.0 mg.ml$^{-1}$ in 25 mM sodium phosphate pH 7.0. Peptide conformation was estimated from spectra using the CONTIN secondary structure analysis computer program (Provencher and Glockner, 1981; Provencher, 1982).

Identification of useful polypeptide emulsifiers and studies of their structure-function relationships started from an 18-amino-acid peptide, Peptide 1, with the sequence Ser-Trp-Ala-Glu-Ala-Leu-Ser-Lys-Leu-Leu-Glu-Ser-Leu-Ala-Lys-Ala-Leu-Ser. The helical wheel representation of this structure (FIG. 1) shows the way the hydrophobic face of the helix was designed to cover 200° of arc with large hydrophobic side chains (Leu and Trp) flanked by smaller hydrophobic side chains (Ala). The hydrophilic Face covers 160° of arc and comprises equal numbers of positively and negatively charged amino acids (identified in the figures by a superscript showing the sign of the charge that they carry) flanked by the small, polar (but uncharged) side chains of serines. When such a molecule is allowed to orient itself at an interface, the large hydrophobic side chains extend deeply into the apolar phase, whereas the charged amino acids are those that are most exposed to the aqueous phase. The alanines and serines are close to the phase interface. The helical net representation of the structure (FIG. 2) shows the way the positive and negative charges were arranged to maximize the number of potential intramolecular salt bridge interactions. It also shows that this sequence can form up to 5 turns of a alpha-helix, assuming that there are 3.6 residues per turn.

Circular dichroism measurements on this peptide confirmed that its conformation was substantially helical in free solution (43% helix in 25 mM sodium phosphate pH 7.0, rising to 59% in the helix promoting solvent, 25% trifluoroethanol (TFE)). The emulsion forming activity of this peptide, as determined by turbidimetry, was exceptional. Its emulsifying activity index was 1.9 times that of bovine serum albumin (BSA) which was the most active natural protein studied by Pearce and Kinsella (1978). This value would also put it well ahead of the succinylated yeast proteins which were the most effective of all the emulsifiers in their study. Oil-in-water emulsions prepared with Peptide 1 were also very stable. At room temperature individual preparations did not start to break for periods ranging from 5-11 days. Once broken, emulsions could be reformed by reprocessing with the Polytron, indicating a remarkable resistance to over-processing compared with natural proteins. At 90° C., stability was similar to that of emulsions prepared with BSA though this was achieved with much less gelling of the aqueous phase. Further evidence for the exceptional surface activity of Peptide 1 was the way that a lot of foaming occurred during emulsification with the Polytron, and that this foam was sufficiently stable, despite the presence of 50% oil, that it took very careful evacuation over several minutes to break it. After allotting time for phase separation, the aqueous phase was not clear but was instead translucent and remained so over a period of months, suggesting the possible presence of thermodynamically-stable microemulsion particles. In fact all the peptides synthesized to date in connection with this study exhibited both this property and the resistance to overprocessing mentioned above in connection with Peptide 1.

Figure 11:
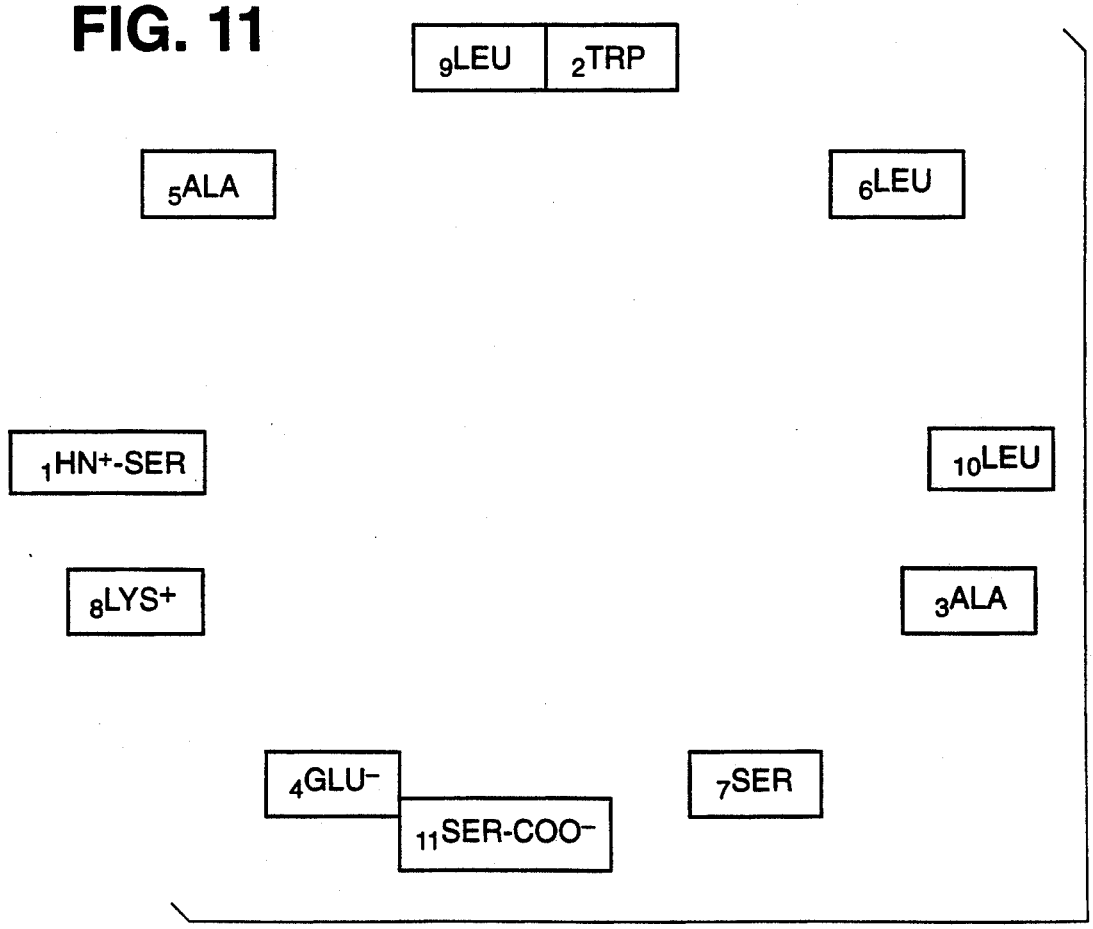
Figure 12:
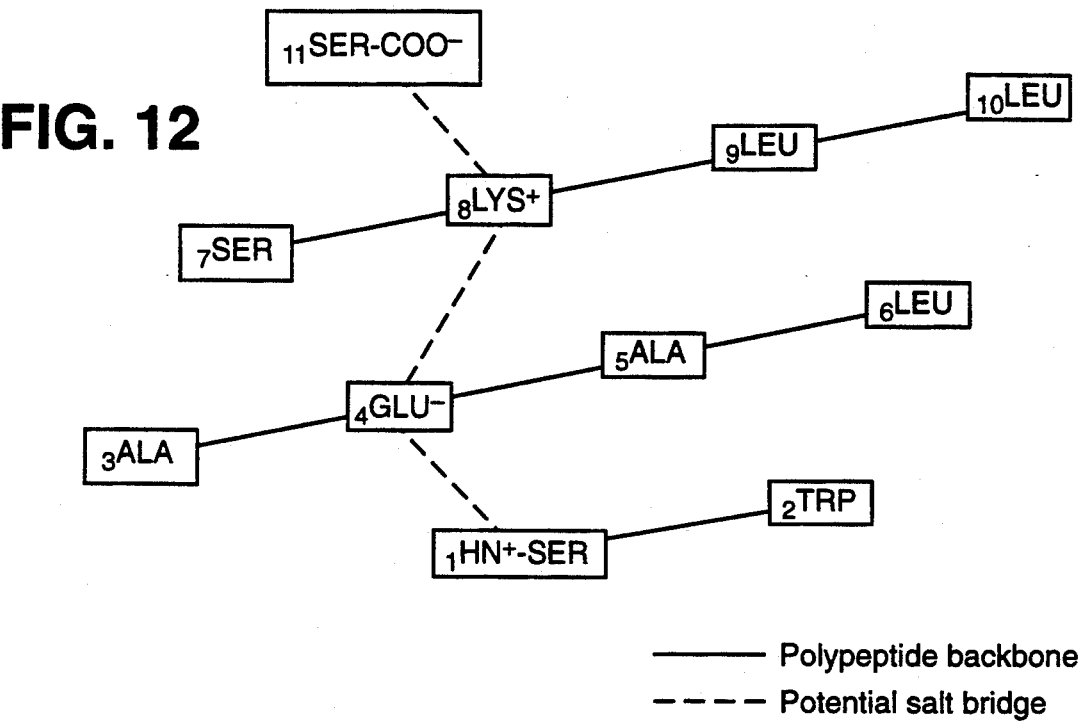
Figure 13:
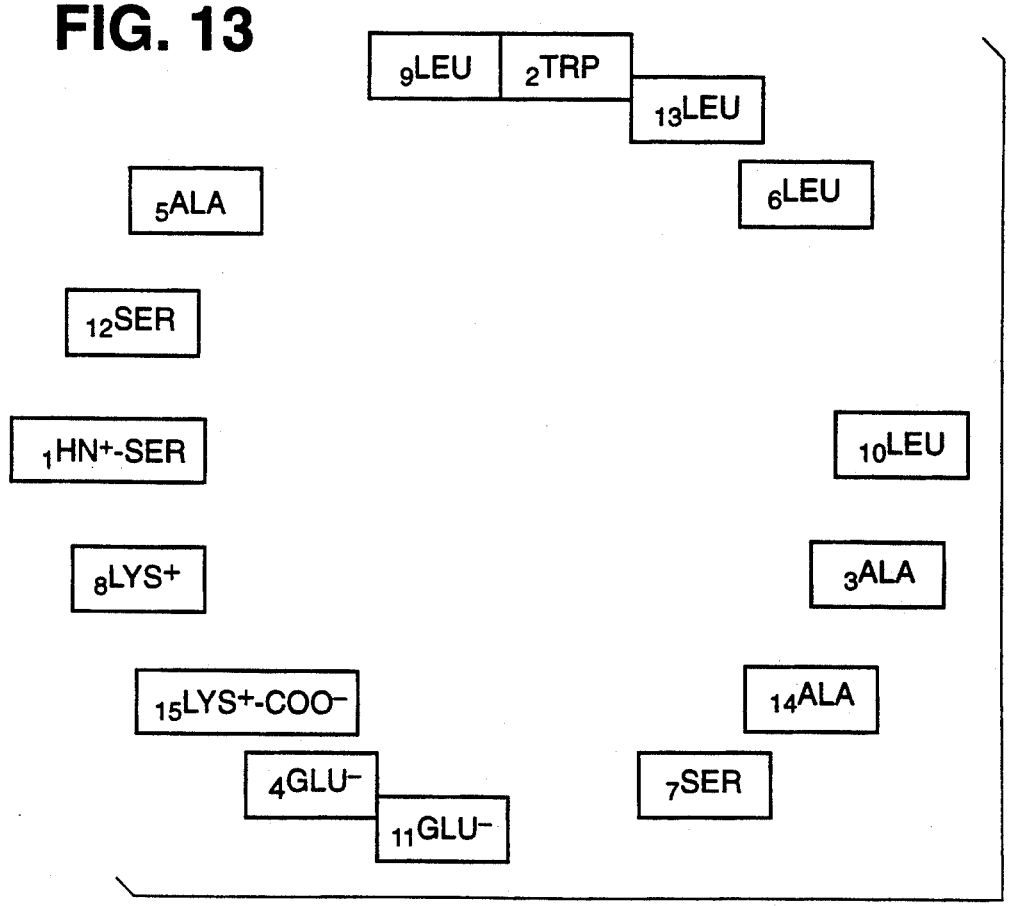
Figure 14:
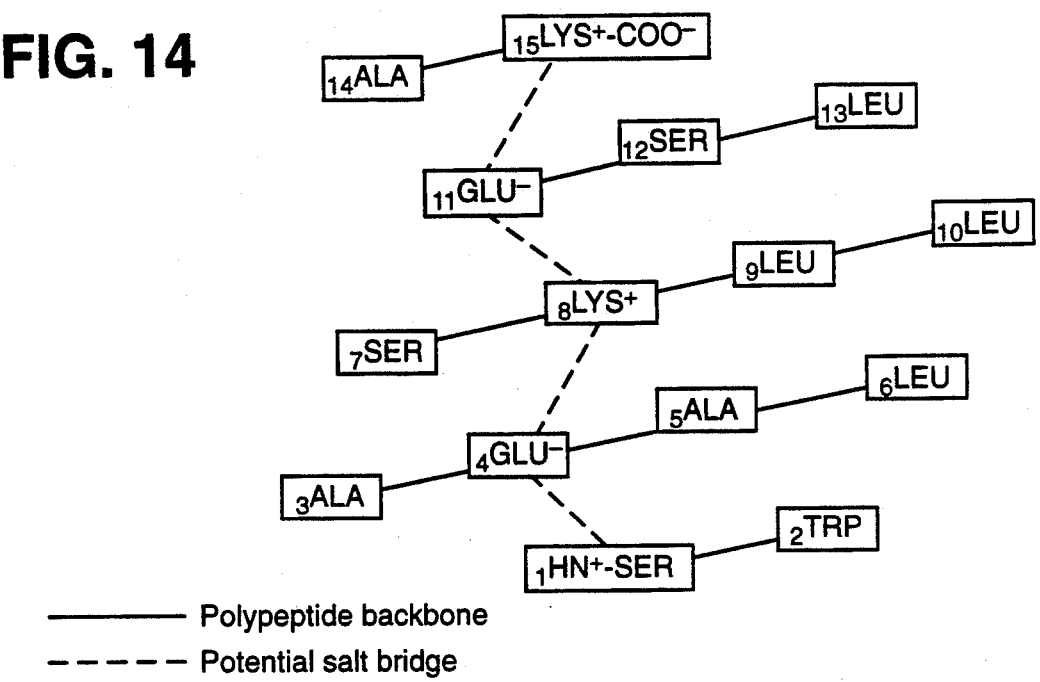

In order to determine the effect of varying polypeptide chain length on its structure and function, the following series of peptides homologous to Peptide 1 were synthesized and studied. Peptide 2 comprised just 8 amino acids, with the sequence Ser-Trp-Ala-Glu-Ala-Leu-Ser-Lys, the same as the amino-terminal 8 residues of Peptide 1. Consequently, the axial view is identical to that of Peptide 1, except that many sites on the helical wheel (FIG. 3) are unoccupied. When drawn as a helical net (FIG. 4), it is also evident that Peptide 2 has a similar arrangement of potential intramolecular salt bridges to the equivalent part of Peptide 1, even though it can only form a maximum of 2 helical turns. Similarly Peptides 6 and 7 comprised 11 and 15 amino acids respectively with the sequences Ser-Trp-Ala-Glu-Ala-Leu-Ser-Lys-Leu-Leu-Ser and Ser-Trp-Ala-Glu-Ala-Leu-Ser-Lys-Leu-Leu-Glu-Ser-Leu-Ala-Lys. These too had similar axial views to Peptide 1 except for unoccupied sites (FIGS. 11 and 13), and homologous salt-bridge networks (FIGS. 12 and 14) within their potential 3 and 4 turns of helix.

Figure 5:
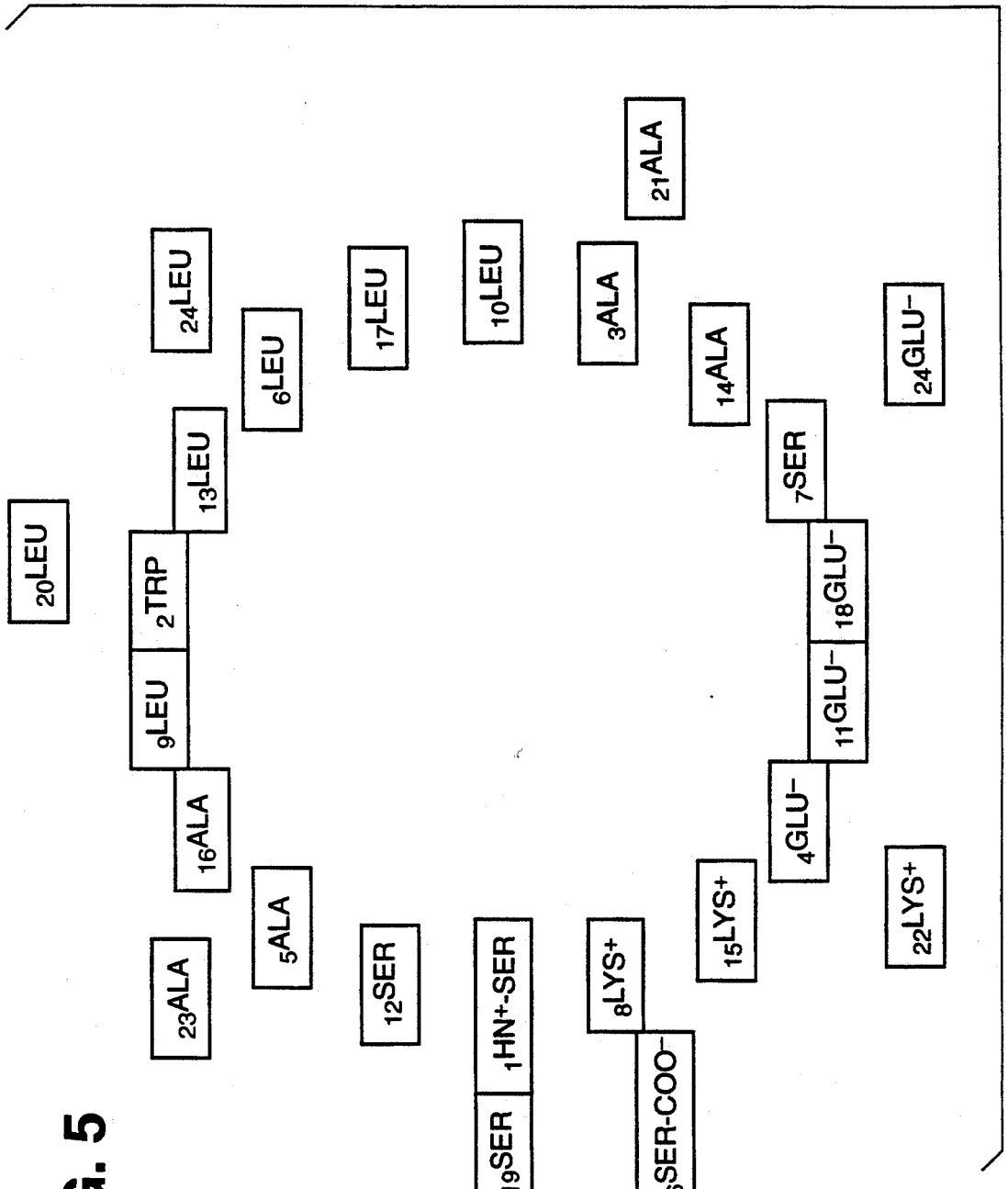
Figure 6:
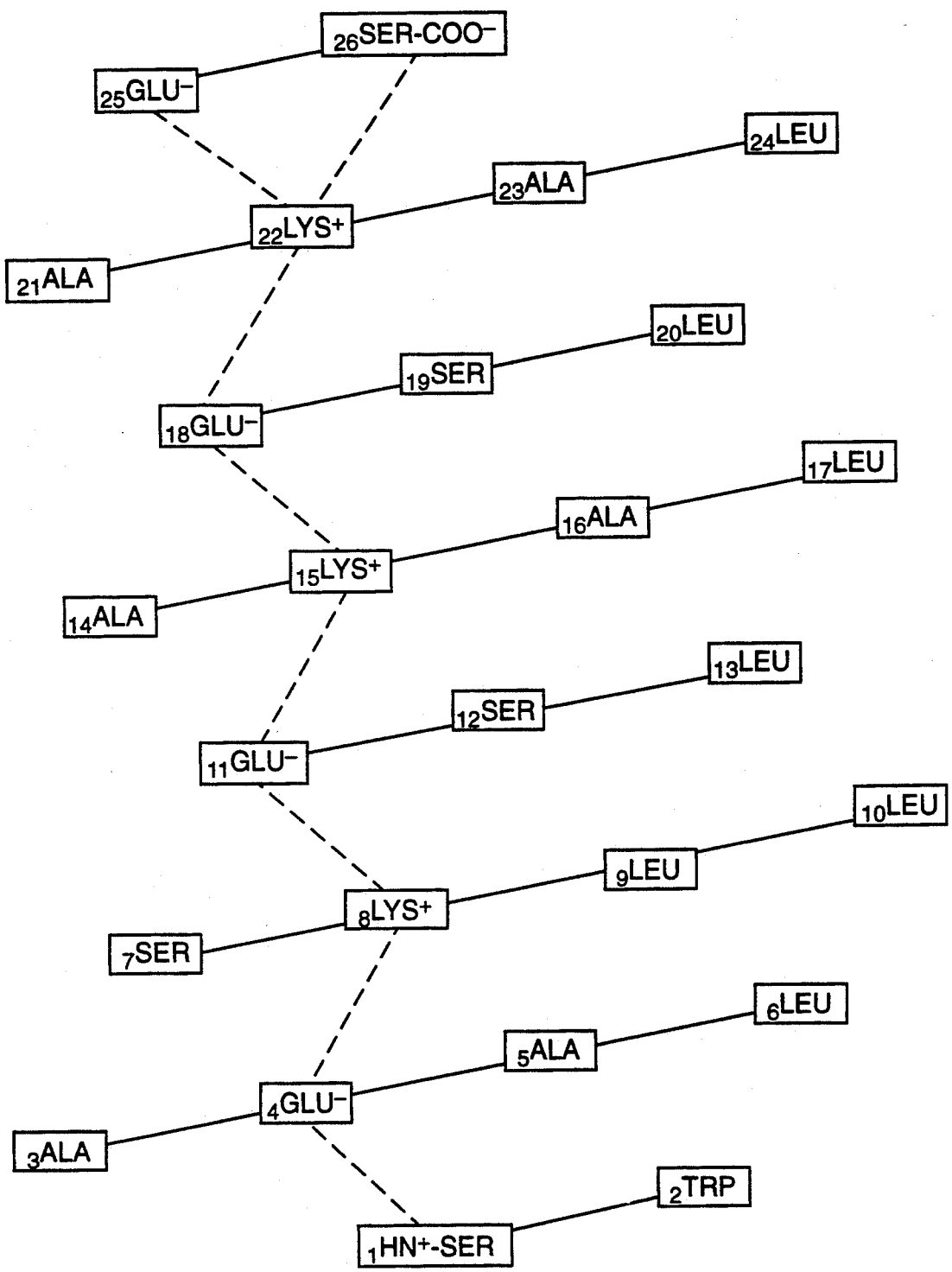

Peptide 3 comprised 26 amino acids, with the sequence Ser-Trp-Ala-Glu-Ala-Leu-Ser-Lys-Leu-Leu-Glu-Ser-Leu-Ala-Lys-Ala-Leu-Glu-Ser-Leu-Ala-Lys-Ala-Leu-Glu-Ser. In this case the amino-terminal 17 residues were identical to Peptide 1, and the helical wheel representation of Peptide 3 (FIG. 5) shows how the design was extended with almost complete conservation of the axial view of the structure. The only difference is a slight widening of the arc occupied by charged amino acids, though this arc still remains entirely confined within the hydrophilic face of the helix, which covers the same proportion of the surface as in Peptide 1. The helical net representation of Peptide 3 (FIG. 6) shows that the arrangement of potential intramolecular salt bridges is conserved, and extended in a similar manner, for all 7 helical turns which are possible in this peptide.

Figure 15:
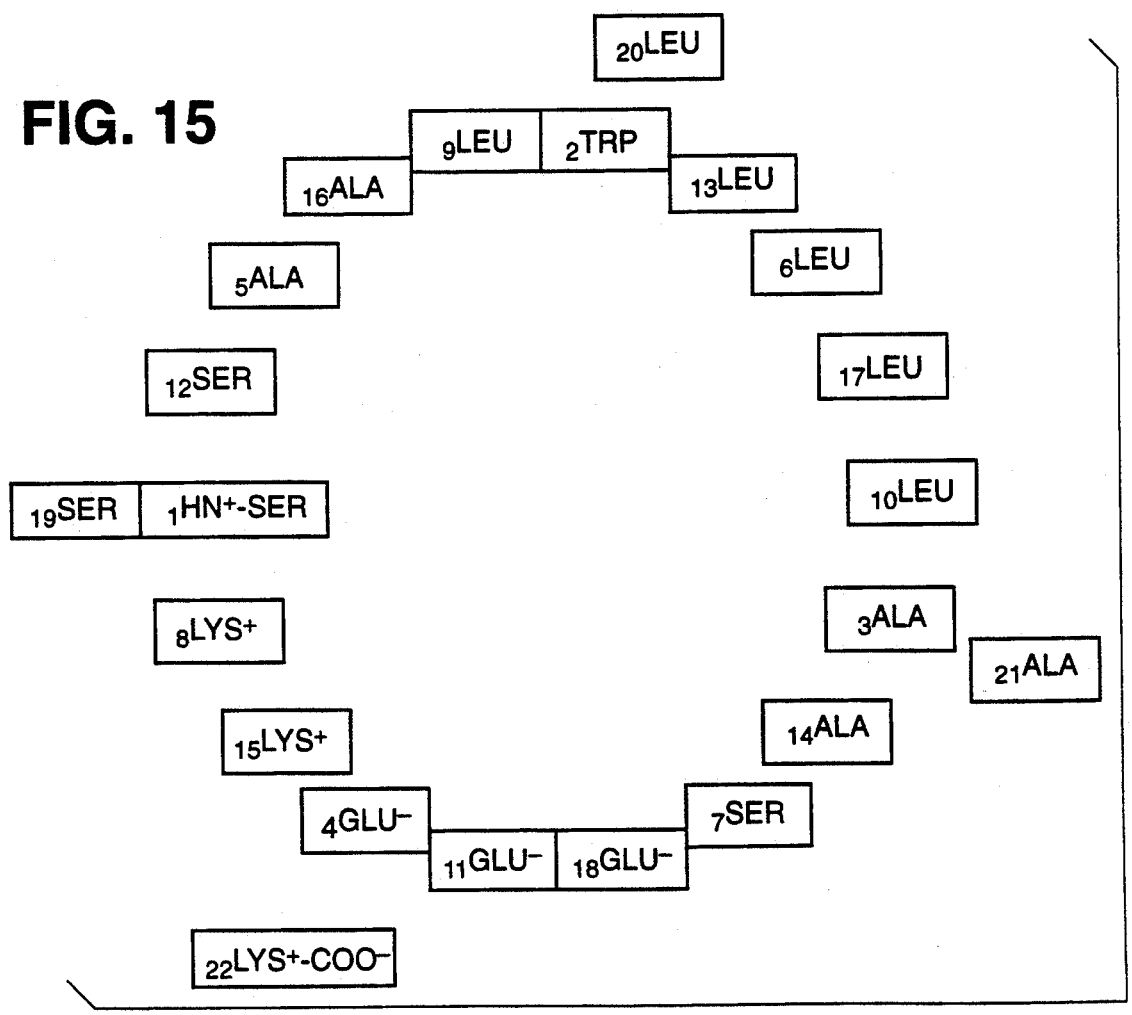
Figure 16:
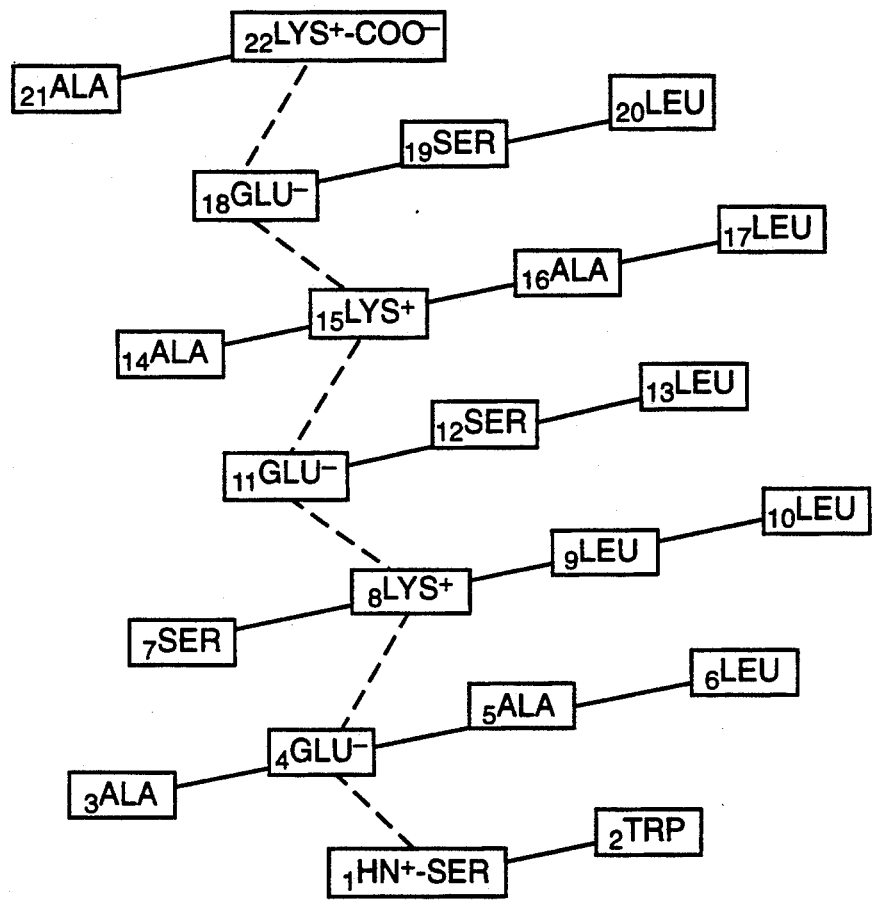
Figure 17:
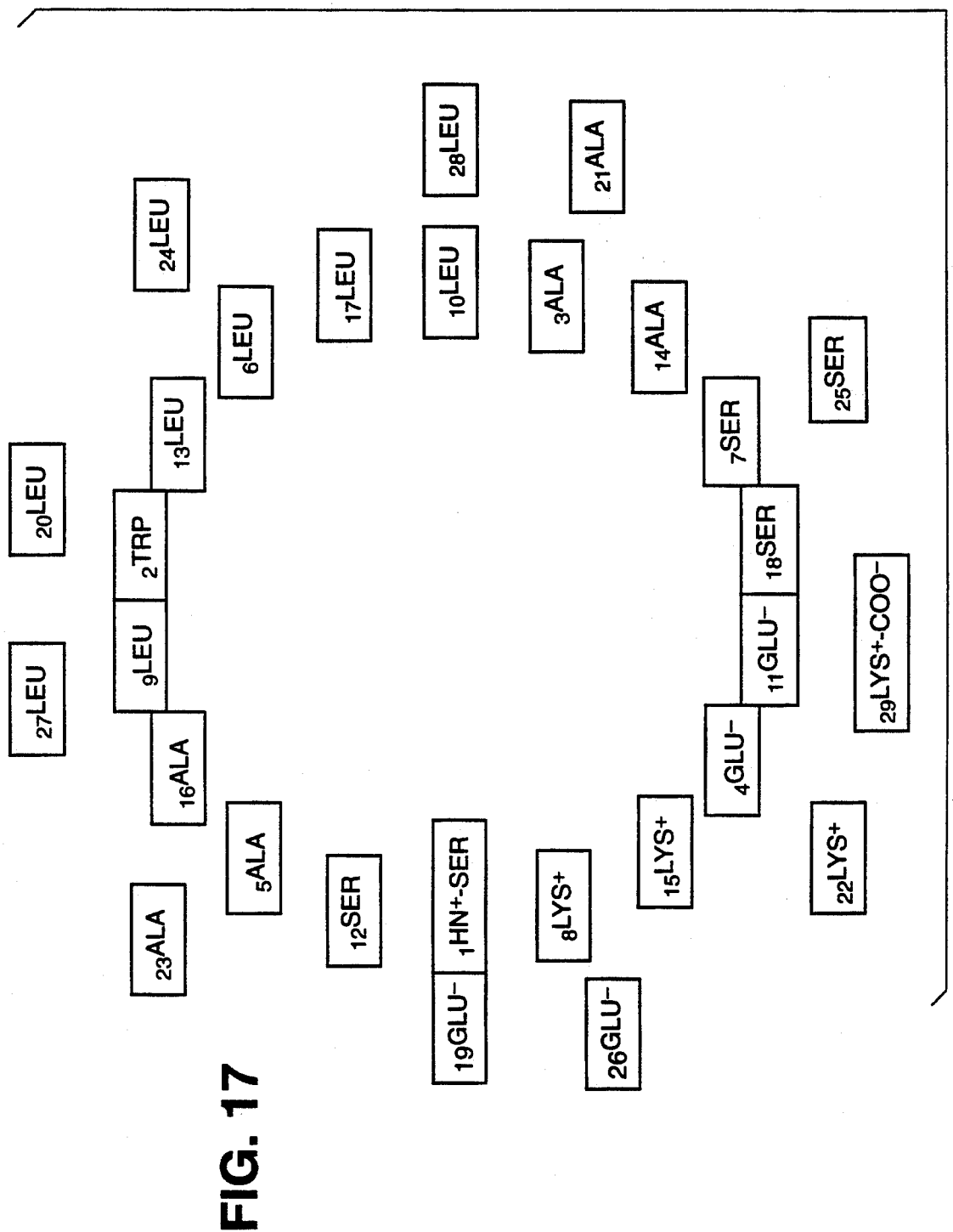
Figure 18:
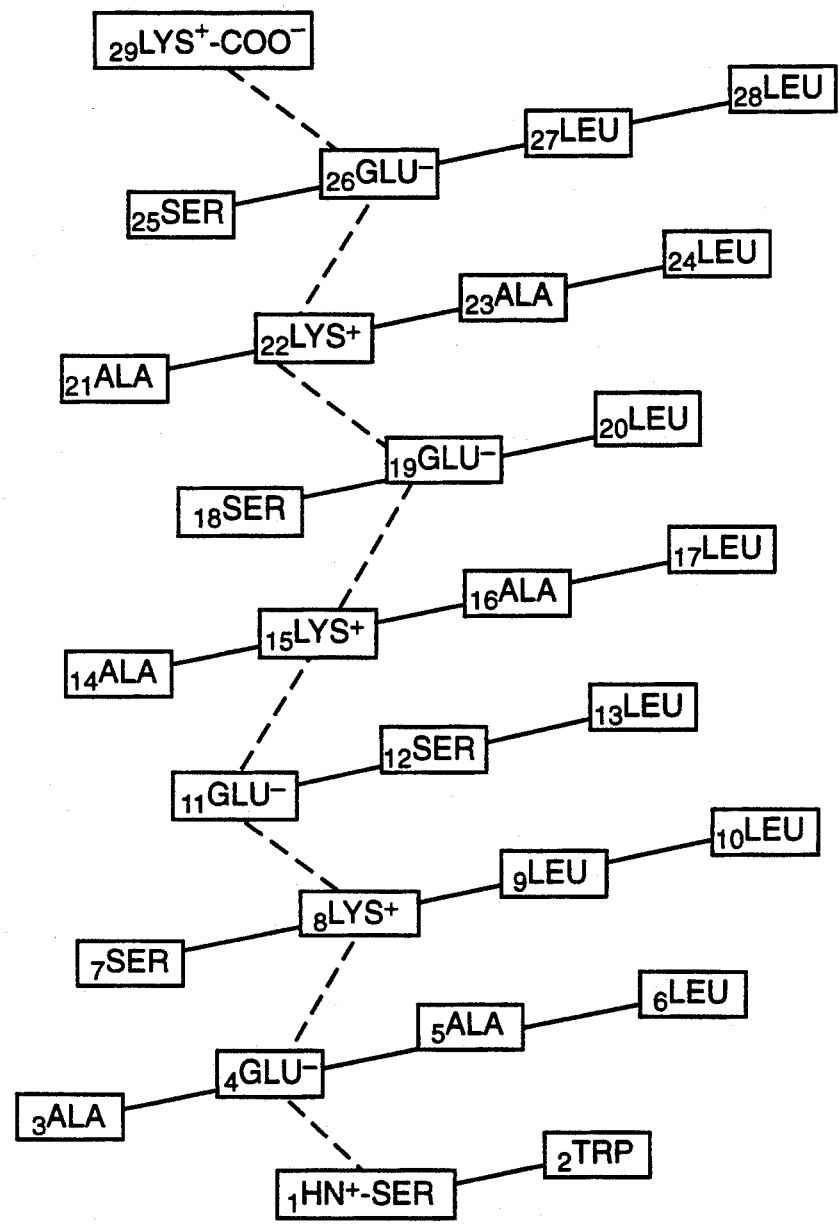
Figure 19:
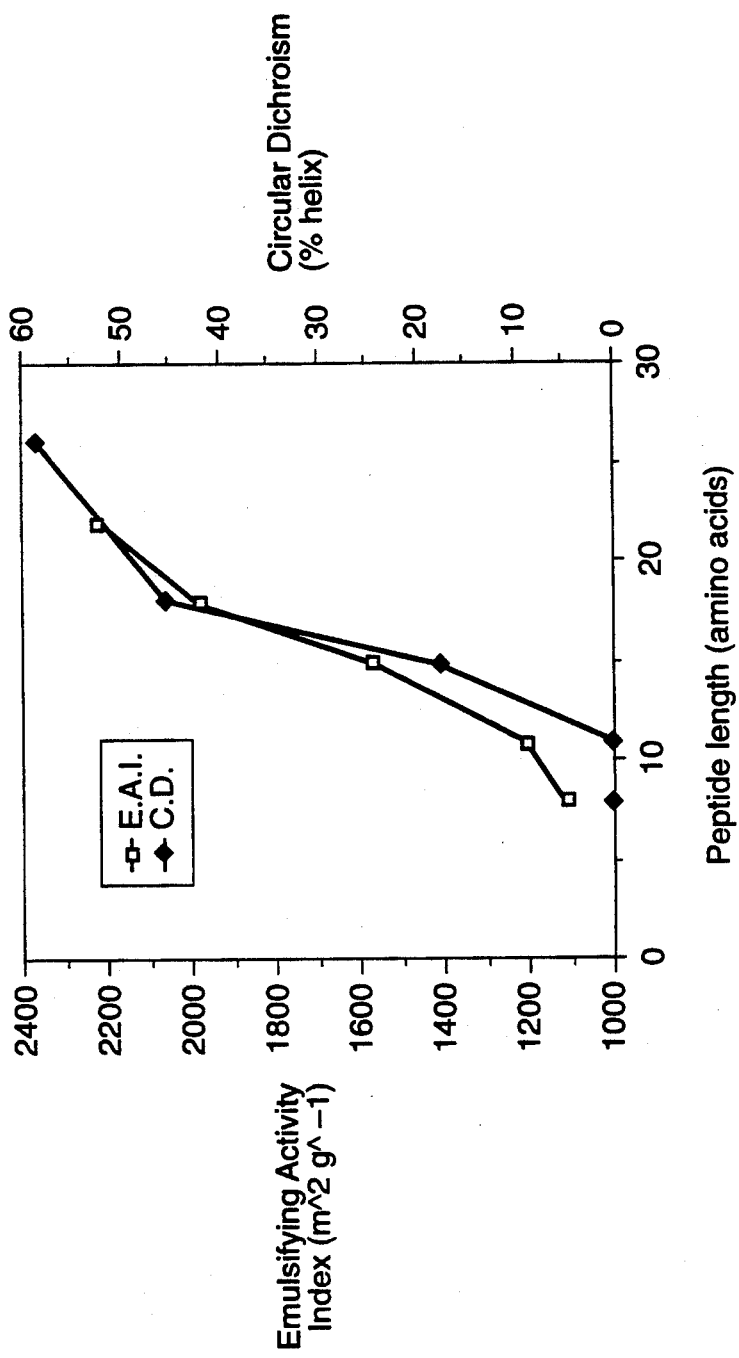
FIG. 19 is a graph of emulsifying activity and helical structure against peptide length.

Peptides 8 and 9 comprised 22 and 29 amino acids respectively with the sequences Ser-Trp-Ala-Glu-Ala-Leu-Ser-Lys-Leu-Leu-Glu-Ser-Leu-Ala-Lys-Ala-Leu-Glu-Ser-Leu-Ala-Lys and Ser-Trp-Ala-Glu-Ala-Leu-Ser-Lys-Leu-Leu-Glu-Ser-Leu-Ala-Lys-Ala-Leu-Ser-Glu-Leu-Ala-Lys-Ala-Leu-Ser-Glu-Leu-Leu-Lys which have the potential to form 6 and 8 alpha-helical turns. Once again the axial distribution of charged, polar and non-polar amino acids is conserved (FIGS. 15 and 17), as is the potential salt bridge network apart from the orientation of one interaction in the longest peptide (FIGS. 16 and 18). Circular dichroism measurements on this series of peptides showed that their solution conformation is crucially affected by their lengths. This is illustrated graphically in FIG. 19 which shows that in purely aqueous buffer the propensity to adopt an alpha-helical conformation increases dramatically for these peptides above about 11 amino acids in length. Concomitant with this there is an equally dramatic increase in their emulsifying activity indices from values comparable with good natural proteins (e.g. BSA, about 1000 m.$^2$g.$^{-1}$ in this system) to the exceptionally high value that was measured for Peptide 1, and above for longer analogues. This is good evidence that the ability to adopt an amphiphathic conformation in purely aqueous solution, rather than having to refold into such a structure upon reaching an interface, enhances surface activity. Furthermore it indicates that our efforts to design peptides with this property have been particularly successful for peptides of this type longer than about 11 amino acids (equivalent to about 3 turns of alpha-helix).

Emulsion stability was sensitive to variations in storage conditions (e.g. room temperature), which meant that the lifetimes of emulsions prepared on different occasions were not strictly comparable. However when emulsions were prepared on the same day with different peptides and stored together, emulsion stability increased consistently with peptide length, typically from 1-3 days for Peptide 2 (8 amino acids) to several weeks for Peptides 3 and 9 (26 and 29 amino acids).

A consistent picture emerges from these experiments. As polypeptide chain length is increased from 2 turns (Peptide 2) to 5 turns (Peptide 1) of helix, helical conformation and emulsion forming and stabilising activities increase rapidly. A further increase in length to 7 turns (Peptide 3) of helix leads to a further more gradual increase in all these properties. Although a general rule is that the longer the polypeptide chain the better is its emulsifying activity, both Peptides 2 and 3 are among the set of structures with exceptional functionality compared with protein and fatty-acid derived emulsifying agents.

Figure 7:
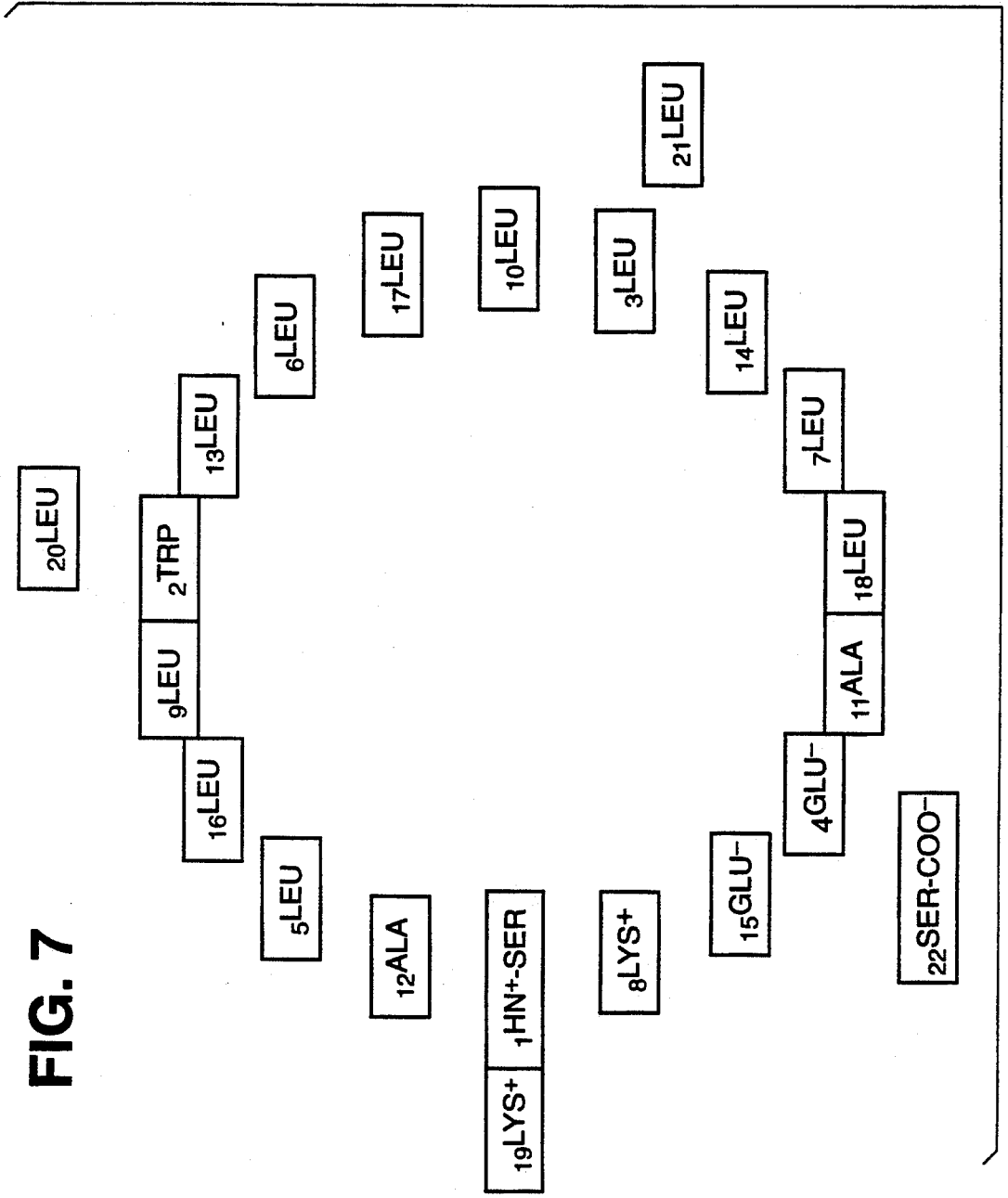
Figure 8:
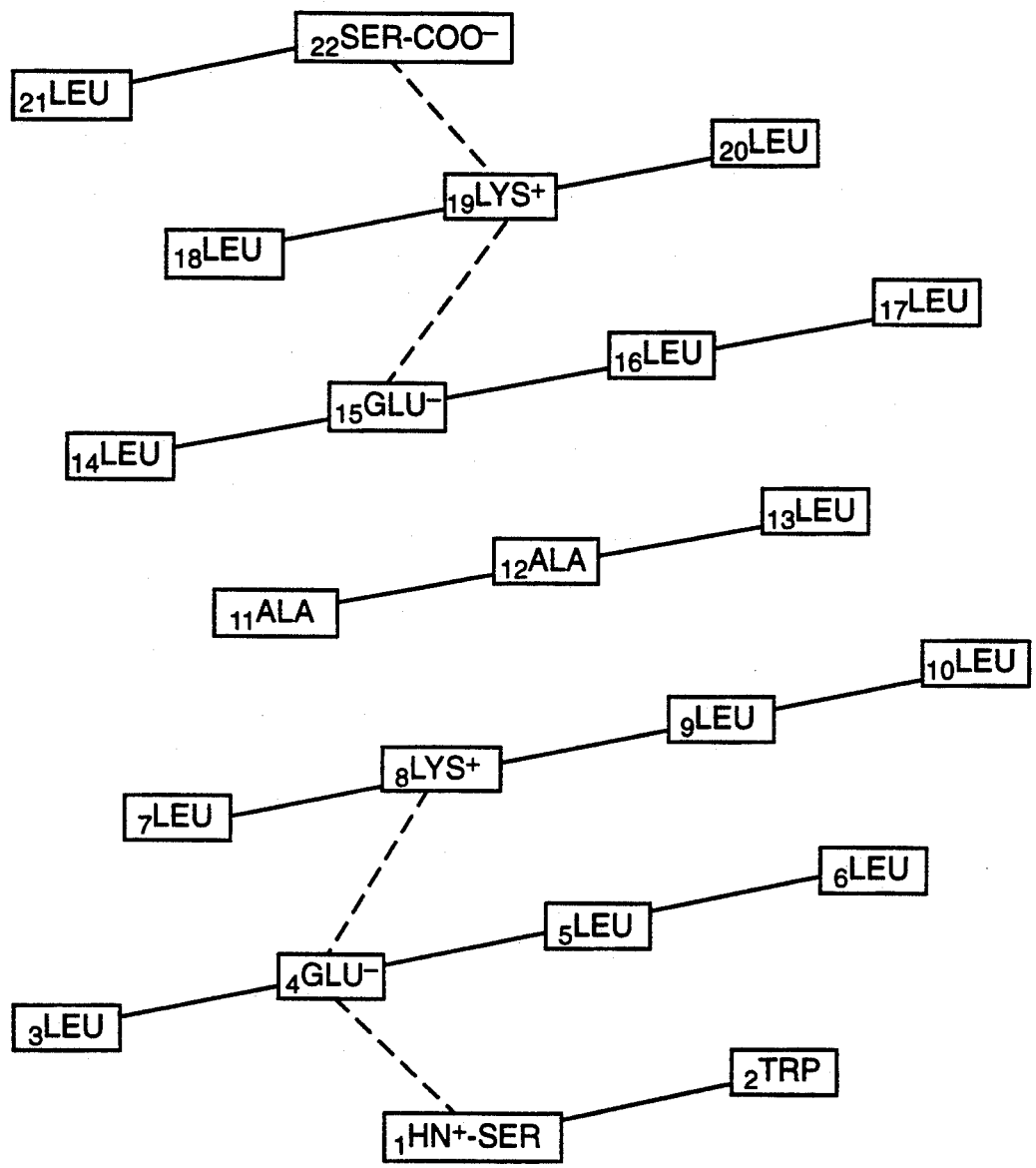
Figure 9:
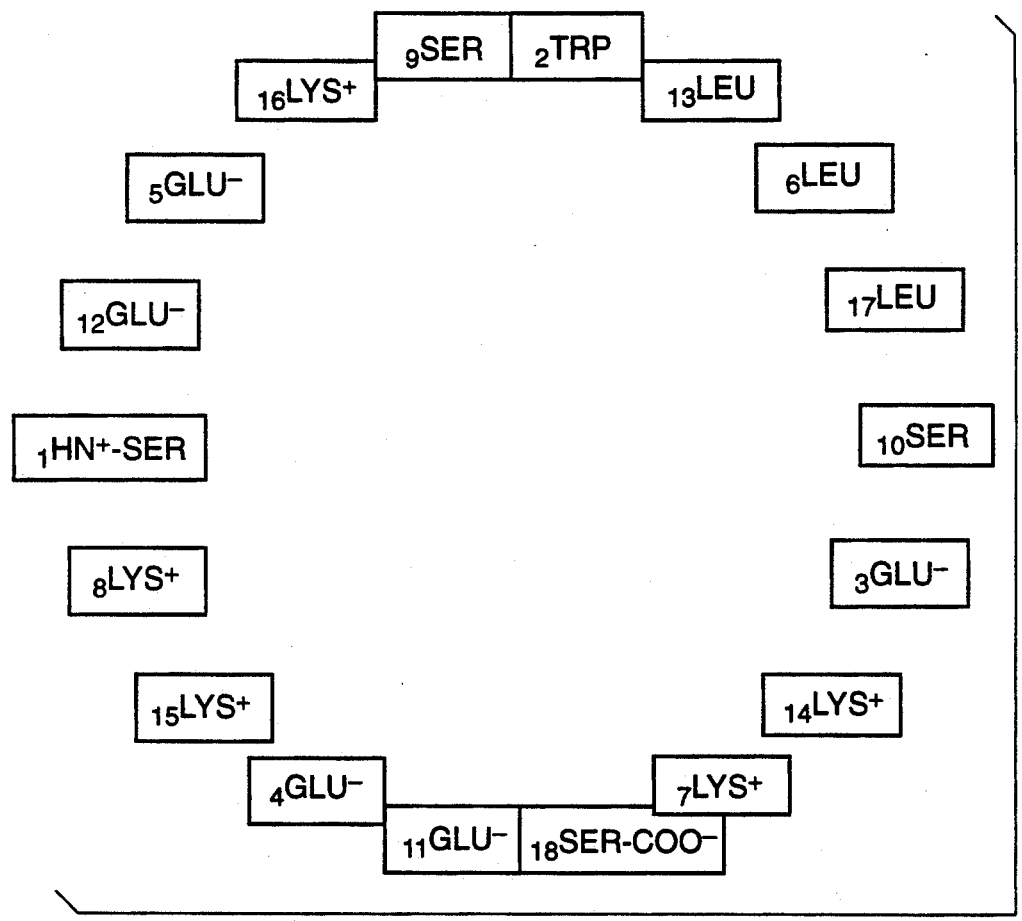
Figure 10:
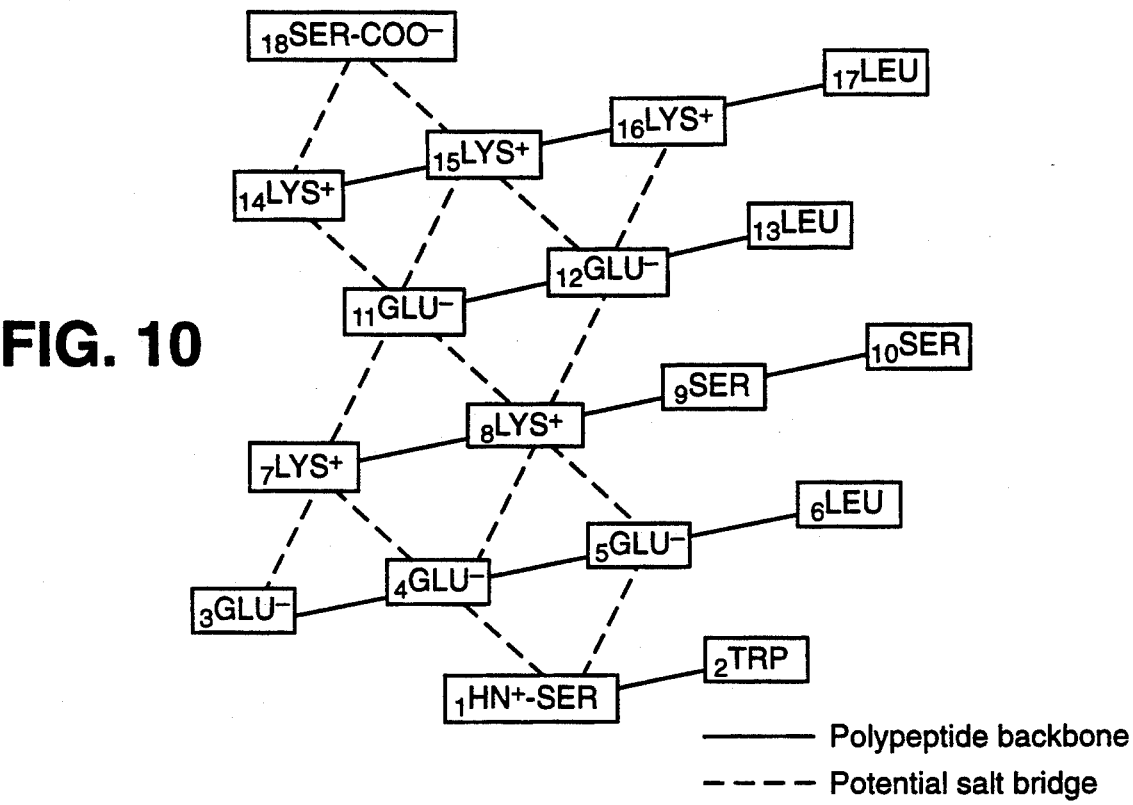

The next structural feature to be varied to study its relationship to functionality was the balance between the hydrophobic and hydrophilic surface areas. Peptides 1-3 all had hydrophobic faces occupying 200° of arc and hydrophilic faces occupying the remaining 160° of arc. Peptide 4 was a 22-residue polypeptide with the sequence Ser-Trp-Leu-Glu-Leu-Leu-Leu-Lys-Leu-Leu-Ala-Ala-Leu-Leu-Glu-Leu-Leu-Lys-Leu-Leu-Ser. It was designed with a large hydrophobic surface, covering 280° of arc, and a narrow hydrophilic face confined to the remaining 80° of arc (FIG. 7). The hydrophilic face was so narrow that it was necessary to populate it entirely with charged amino acids in order to retain a vestigial salt-bridge network (FIG. 8) which was in any way similar to the other peptides. The converse of this was the 18-residue Peptide 5 with the sequence Ser-Trp-Glu-Glu-Glu-Leu-Lys-Lys-Ser-Ser-Glu-Glu-Leu-Lys-Lys-Lys-Leu-Ser. The hydrophobic face of this peptide was confined to 80° of arc while the hydrophilic face occupied 280° of arc (FIG. 9). With such a narrow hydrophobic face it was decided to fill it with large hydrophobic side chains. However, this peptide's most notable feature is on the hydrophilic face, where the network of potential salt bridges is extended in an additional dimension, from its almost linear arrangement in the other peptides, to a sheet-like network (FIG. 10). This is to stabilize its helical conformation to the maximum extent, because even when oriented at an interface such a molecule is likely to be extensively solvated.

Peptide 5 (18 amino acids) exhibited emulsion-forming activity that was intermediate between the values for Peptide 1 (18 amino acids) and Peptide 3 (26 amino acids). Its circular dichroism spectrum indicated no alpha-helical structure in purely aqueous solution, but it exhibited a remarkable propensity to adopt such a conformation in helix-promoting conditions (e.g. 35% helix in 50% TFE). This was a much greater enhancement than other peptides showed in such a solvent and is likely to be indicative of its behaviour at an interface, which would be an extremely helix-promoting environment.

Peptide 4 (22 amino acids) was difficult to handle because of its extreme hydrophobicity, so circular dichroism spectra are not yet available for it. Its emulsifying activity was similar to that of somewhat larger peptides, and it produced the most stable (about 2 months) emulsions of all the peptides yet studied. It also had a tendency to form some water-in-oil emulsion as well as the more usual oil-in-water emulsion.

Figure 2:
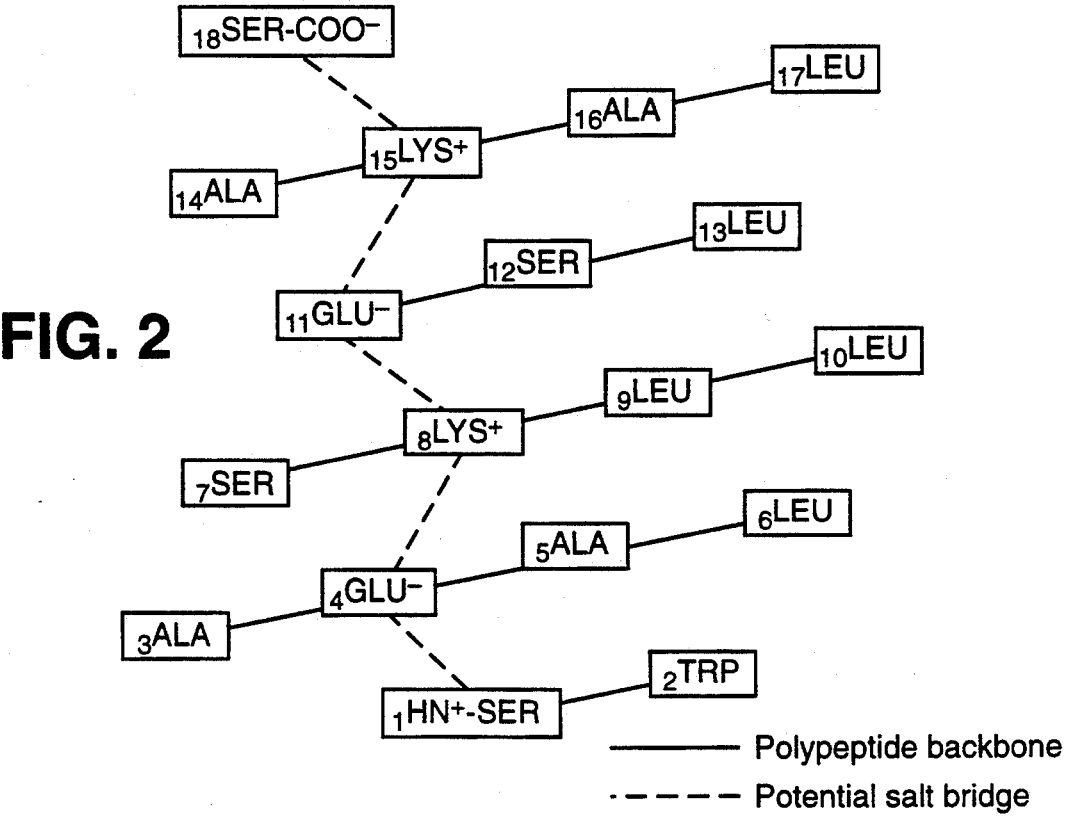

The respective arcs occupied by hydrophobic and hydrophilic amino acids, as viewed in an end-on view such as FIG. 1, were further varied by producing Peptides 10 to 13, the structures of which are given above. Peptides 5, 10, 11, 1, 12, 4 and 13 form a series in which these arcs are respectively 80:280, 120:240. 160:200, 200:160, 240:120, 280:80 and 320:40. It was found that an increase in the hydrophobicity of the peptide caused it to stabilise emulsions highly effectively, without substantial loss of ability to form an emulsion.

However, it does seem likely that the more hydrophobic of such peptides may have even more remarkable interfacial properties than the first series of peptides (Peptides 1, 2, 3, 6, 7, 8, and 9), especially with regard to stabilization and utility in connection with water-in-oil emulsions.

Further peptides were synthesized, based on Peptide 1 but having substitutions of amino acids of the same type.

The peptides have the following sequences:

(14) $NH_2$-Ser-Trp-Ala-Glu-Ala-Leu-Ser-Arg-Leu-Leu-Glu-Ser-Leu-Ala-Arg-Ala-Leu-Ser-COOH (Basic: both Lys residues of Peptide 1 have been substituted by Arg)

(15) $NH_2$-Ser-Trp-Ala-Glu-Ala-Leu-Ser-His-Leu-Leu-Glu-Ser-Leu-Ala-His-Ala-Leu-Ser-COOH (Basic: both Lys substituted by His)

(16) $NH_2$-Ser-Trp-Ala-Asp-Ala-Leu-Ser-Lys-Leu-Leu-Asp-Ser-Leu-Ala-Lys-Ala-Leu-Ser-COOH (Acidic: both Glu substituted by Asp)

(17) $NH_2$-Thr-Trp-Ala-Glu-Ala-Leu-Thr-Lys-Leu-Leu-Glu-Thr-Leu-Ala-Lys-Ala-Leu-Thr-COOH (Uncharged hydrophilic: all four Set substituted by Thr)

The examples depicted above and below are intended to serve to illustrate the invention. The invention is not intended to be limited to the exact examples shown. Other examples or equivalents will suggest themselves to those skilled in the art.

(18) $NH_2$-Gln-Trp-Ala-Glu-Ala-Leu-Gln-Lys-Leu-Leu-Glu-Gln-Leu-Ala-Lys-Ala-Leu-Gln-COOH (Uncharged hydrophilic: all four Set substituted by Gln)

(19) $NH_2$-Asn-Trp-Ala-Glu-Ala-Leu-Asn-Lys-Leu-Leu-Glu-Asn-Leu-Ala-Lys-Ala-Leu-Asn-COOH (Uncharged hydrophilic: all four Set substituted by Asn)

(20) $NH_2$-Met-Trp-Ala-Glu-Ala-Leu-Met-Lys-Leu-Leu-Glu-Met-Leu-Ala-Lys-Ala-Leu-Met-COOH (Uncharged hydrophilic: all four Set substituted by Met)

(21) $NH_2$-Cys-Trp-Ala-Glu-Ala-Leu-Cys-Lys-Leu-Leu-Glu-Cys-Leu-Ala-Lys-Ala-Leu-Cys-COOH (Uncharged hydrophilic: all four Set substituted by Cys)

(22) $NH_2$-Ser-Trp-Gly-Glu-Gly-Leu-Ser-Lys-Leu-Leu-Glu-Ser-Leu-Ala-Lys-Gly-Leu-Ser-COOH (Small hydrophobic: all four Ala substituted by Gly)

(23) $NH_2$-Ser-Trp-Ala-Glu-Ala-Val-Ser-Lys-Val-Val-Glu-Ser-Val-Ala-Lys-Ala-Val-Ser-COOH (Large hydrophobic: all five Leu substituted by Val; Trp left in place)

(24) $NH_2$-Ser-Trp-Ala-Glu-Ala-Ile-Ser-Lys-Ile-Ile-Glu-Ser-Ile-Ala-Lys-Ala-Ile-Ser-COOH (Large hydrophics: all five Leu substituted by Ile; Trp left in place)

(25) $NH_2$-Ser-Trp-Ala-Glu-Ala-Phe-Ser-Lys-Phe-Phe-Glu-Ser-Phe-Ala-Lys-Ala-Phe-Ser-COOH (Large hydrophobic: all five Leu substituted by Phe: Trp left in place)

(26) $NH_2$-Ser-Trp-Ala-Glu-Ala-Trp-Ser-Lys-Trp-Trp-Glu-Ser-Trp-Ala-Lys-Ala-Trp-Ser-COOH (Large hydrophobic: all five Leu substituted by Trp)

(27) $NH_2$-Thr-Trp-Gly-Asp-Gly-Ile-Thr-Arg-Ile-Ile-Asp-Thr-Ile-Gly-Arg-Gly-Ile-Thr-COOH (all types changed)

(28) $NH_2$-Tyr-Trp-Tyr-Glu-Tyr-Phe-Tyr-Lys-Phe-Phe-Glu-Tyr-Phe-Tyr-Lys-Tyr-Phe-Tyr-COOH (all unchanged side chains aromatic).

Peptide 26 produces particularly large amounts of foam. Peptides 13, 25 and 26 appear to produce especially stable emulsions (18 to 41 days).

REFERENCES

Dunhill, P. (1968) The use of helical net-diagrams to represent protein structures. Biophys. J. 8, 865–875.

Kaiser, E., Colescott, R. L., Bossinger, C. D. and Cook, P.I. (1970) Color test for detection of free terminal amino groups in the solid-phase synthesis of peptides. Anal. Biochem. 34, 595–598.

Kaiser, E. T. and Kezdy, F. J. (1984) Amphiphilic secondary structure: Design of peptide hormones. Science (Wash. D.C.) 223, 249–255.

Kennedy, S. J. (1978) Structures of membrane proteins. J. Membrane Biol. 42, 265–279.

Pearce, K. N. and Kinsella, J. E. (1978) Emulsifying properties of proteins: Evaluation of a turbidimetric technique. J. Agric. Food Chem. 26, 716–723.

Provencher, S. W. and Glockner, J. (1981) Estimation of globular protein secondary structure from circular dichroism. Biochemistry 20, 33–37.

Provencher, S. W. (1982) CONTIN: A constrained regularization method for inverting noisy linear algebraic and linear equations. Comput. Phys. Commun. 27, 229–242.

Schiller, M. and Edmundson, A. B. (1967) Use of helical wheels to represent the structures of proteins and to identify segments with helical potential. Biophys. J. 7, 121–135.

ABBREVIATIONS

BSA; Bovine serum albumin, SDS; Sodium dodecyl sulphate,
TFE; Trifluoroethanol

We claim:

1. A method for the production of an emulsified product consisting essentially of
adding to a material to be emulsified a polypeptide consisting of not more than 29 amino acid groups having at least one alpha-helical region said alpha-helix having hydrophilic and hydrophobic axial domains such that the axial region of the polypeptide may lie on a fat/water interferace of the product with the hydrophilic axial domain in the water phase and the hydrophobic axial domain in the fat phase, the alpha-helix having at least 2 turns and wherein at least 70% of the amino acids of the polypeptide are in the alpha-helix forming region.

2. The method of claim 1 wherein the entire polypeptide is capable of lying along the fat/water interface of the product with the hydrophilic axial domain in the water phase and the hydrophobic axial domain in the fat phase.

3. The method of claim 1 or 2 wherein there is only one hydrophobic axial domain, one hydrophilic axial domain and no axial domains of intermediate polarity.

4. The method of claim 3 wherein the hydrophobic axial domain occupies 80° C. to 280° of the circle defined by the helix.

5. The method of claim 4 wherein the hydrophobic axial domain occupies at least 180° of the circle.

6. The method of claim 5 wherein the hydrophobic axial domain occupies at least 240° of the circle.

7. The method of claims 1 or 2 wherein the amino acids in the hydrophobic axial domain contribute to the stabilization of the overall configuration by hydrophobic interactions.

8. The method of claims 1 or 3 wherein the hydrophilic amino acids form intramolecular salt bridges which are 3 or 4 residues apart.

9. The method of claims 1 or 2 wherein at least 80% of the backbone amino acids are in a helix-forming sequence.

10. The method of claims 1 or 2 wherein there are at least 11 amino acids in the peptide and the alpha-helix has at least 4 turns.

11. The process of claim 1 consisting essentially of a product selected from the group consisting of foods, pharmaceuticals, cosmetics, cleansers and biosensors.

12. The method of claim 1 consisting substantially of adding a polypeptide selected from at least one of the group consisting of:

(1)   $NH_2$-Ser-Trp-Ala-Glu-Ala-Leu-Ser-Lys-Leu-Leu-Glu-Ser-Leu-Ala-Lys-Ala-Leu-Ser-COOH, (2) $NH_2$-Ser-Trp-Ala-Glu-Ala-Leu-Ser-Lys-COOH, (3)   $NH_2$-Ser-Trp-Ala-Glu-Ala-Leu-Ser-Lys-Leu-Leu-Glu-Ser-Leu-Ala-Lys-Ala-Leu-Glu-Ser-Leu-Ala-Lys-Ala-Leu-Glu-Ser-COOH, (4)   $NH_2$-Ser-Trp-Leu-Glu-Leu-Leu-Leu-Lys-Leu-Leu-Ala-Ala-Leu-Leu-Glu-Leu-Leu-Leu-Lys-Leu-Leu-Ser-COOH, (5)   $NH_2$-Ser-Trp-Glu-Glu-Leu-Lys-Lys-Ser-Ser-Glu-Glu-Leu-Lys-Lys-Lys-Leu-Ser-COOH, (6)   $NH_2$-Ser-Trp-Ala-Glu-Ala-Leu-Ser-Lys-Leu-Leu-Ser-COOH, (7)   $NH_2$-Ser-Trp-Ala-Glu-Ala-Leu-Ser-Lys-Leu-Leu-Glu-Ser-Leu-Ala-Lys-COOH, (8)   $NH_2$-Ser-Trp-Ala-Glu-Ala-Leu-Ser-Lys-Leu-Leu-Glu-Ser-Leu-Ala-Lys-Ala-Leu-Glu-Ser-Leu-Ala-Lys-COOH, (9)   $NH_2$-Ser-Trp-Ala-Glu-Ala-Leu-Ser-Lys-Leu-Leu-Glu-Ser-Leu-Ala-Lys-Ala-Leu-Ser-Glu-Leu-Ala-Lys-Ala-Leu-Ser-Glu-Leu-Leu-Lys-COOH,

(10)   $NH_2$-Ser-Trp-Ser-Glu-Glu-Leu-Lys-Lys-Ala-Ala-Glu-Glu-Leu-Lys-Lys-Ser-Leu-Ser-COOH,

(11)   $NH_2$-Ser-Trp-Ala-Glu-Ser-Leu-Lys-Lys-Ala-Ala-Glu-Glu-Leu-Ser-Lys-Ala-Leu-Ser-COOH,

(12)   $NH_2$-Ser-Trp-Leu-Glu-Ala-Leu-Ala-Lys-Leu-Leu-Ser-Ser-Leu-Ala-Glu-Ala-Leu-Ala-Lys-Leu-Leu-Ser-COOH,

(13)   $NH_2$-Ser-Trp-Leu-Ala-Ala-Leu-Leu-Glu-Leu-Leu-Ala-Leu-Leu-Ala-Leu-Leu-Leu-Lys-COOH,

(14)   $NH_2$-Ser-Trp-Ala-Glu-Ala-Leu-Ser-Arg-Leu-Leu-Glu-Ser-Leu-Ala-Arg-Ala-Leu-Ser-COOH,

(15)   $NH_2$-Ser-Trp-Ala-Glu-Ala-Leu-Ser-His-Leu-Leu-Glu-Ser-Leu-Ala-His-Ala-Leu-Ser-COOH,

(16)   $NH_2$-Ser-Trp-Ala-Asp-Ala-Leu-Ser-Lys-Leu-Leu-Asp-Ser-Leu-Ala-Lys-Ala-Leu-Ser-COOH,

(17)   $NH_2$-Thr-Trp-Ala-Glu-Ala-Leu-Thr-Lys-Leu-Leu-Glu-Thr-Leu-Ala-Lys-Ala-Leu-Thr-COOH,

(18)   $NH_2$-Gln-Trp-Ala-Glu-Ala-Leu-Gln-Lys-Leu-Leu-Glu-Gln-Leu-Ala-Lys-Ala-Leu-Gln-COOH,

(19)   $NH_2$-Asn-Trp-Ala-Glu-Ala-Leu-Asn-Lys-Leu-Leu-Glu-Asn-Leu-Ala-Lys-Ala-Leu-Asn-COOH,

(20)   $NH_2$-Met-Trp-Ala-Glu-Ala-Leu-Met-Lys-Leu-Leu-Glu-Met-Leu-Ala-Lys-Ala-Lys-Ala-Leu-MEt-COOH,

(21)   $NH_2$-Cys-Trp-Ala-Glu-Ala-Leu-Cys-Lys-Leu-Leu-Glu-Cys-Leu-Ala-Lys-Ala-Leu-Cys-COOH,

(22)   $NH_2$-Ser-Trp-Gly-Glu-Gly-Leu-Ser-Lys-Leu-Leu-Glu-Ser-Leu-Gly-Lys-Gly-Leu-Ser-COOH,

(23)   $NH_2$-Ser-Trp-Ala-Glu-Ala-Val-Ser-Lys-Val-Val-Glu-Ser-Val-Ala-Lys-Ala-Val-Ser-COOH,

(24) NH$_2$-Ser-Trp-Ala-Glu-Ala-Ile-Ser-Lys-Ile-Ile-Glu-Ser-Ile-Ala-Lys-Ala-Ile-Ser-COOH,
(25) NH$_2$-Ser-Trp-Ala-Glu-Ala-Phe-Ser-Lys-Phe-Phe-Glu-Ser-Phe-Ala-Lys-Ala-Phe-Ser-COOH,
(26) NH$_2$-Ser-Trp-Ala-Glu-Ala-Trp-Ser-Lys-Trp-Trp-Glu-Ser-Trp-Ala-Lys-Ala-Trp-Ser-COOH,
(27) NH$_2$-Thr-Trp-Gly-Asp-Gly-Ile-Thr-Arg-Ile-Ile-Asp-Thr-Ile-Gly-Arg-Gly-Ile-Thr-COOH,
(28) NH$_2$-Tyr-Trp-Tyr-Glu-Tyr-Phe-Tyr-Lys-Phe-Phe-Glu-Tyr-Phe-Tyr-Lys-Tyr-Phe-Tyr-COOH, and variants thereof wherein (i) Glu and Gln are interchangeable, (ii) Asp and Ash are interchangeable, (iii) there are up to two non-helix-forming amino acids at each end of the peptide (iv) Lys and Arg are interchangeable, (v) Lys and His are interchangeable, (vi) Set and Thr are interchangeable (vii) Glu and Asp are interchangeable, (viii) Set and Gln are interchangeable, (ix) Set and Ash are interchangeable, (x) Set and Met are interchangeable, (xi) Ser and Cys are interchangeable, (xii) Ala and Gly are interchangeable, (xiii) Leu and Val are interchangeable, (xiv) Leu and Ile are interchangeable, (xv) Leu and Phe are interchangeable, (xvi) Leu and Trp are interchangeable, (xvii) all aromatic side chains (xiii) hydrophobic and hydrophilic amino acids are interchangeable.

* * * * *

UNITED STATES PATENT AND TRADEMARK OFFICE
CERTIFICATE OF CORRECTION

PATENT NO. : 5,330,682
DATED : July 19, 1994
INVENTOR(S) : Christopher J. Brock, et al.

It is certified that error appears in the above-indentified patent and that said Letters Patent is hereby corrected as shown below:

Col. 6, line 4: change "CAR" to -- CRB --.

Col. 6, line 47: change "destabilize" to -- destabilized --.

Col. 6, line 51: change "J-B600" to -- J-600 --.

Col. 10, lines 21, 30, 35, 39 and 43: change "Set" to -- Ser --.

Col. 10, line 36: change "Ash" to -- Asn --.

Col. 10, line 46: change "Ala" to -- Gly --.

Col. 12, line 1
    Claim 8: delete "3" and insert -- 2 --.

Col. 12, line 62
    Claim 12: change "MEt" to -- Met --.

Col. 13, line 12
    Claim 12: change "Ash" to -- Asn --.

Col. 14, line 3: change "Set" to -- Ser --.

Col. 14, line 4: change "Set" to -- Ser -- and change "Ash" to -- Asn --.

UNITED STATES PATENT AND TRADEMARK OFFICE
CERTIFICATE OF CORRECTION

PATENT NO. : 5,330,682
DATED : July 19, 1994
INVENTOR(S) : Christopher J. Brock, et al.

It is certified that error appears in the above-indentified patent and that said Letters Patent is hereby corrected as shown below:

Col. 14, line 5: change "Set" to -- Ser --.

Signed and Sealed this

Sixth Day of December, 1994

*Attest:*

BRUCE LEHMAN

*Attesting Officer*        *Commissioner of Patents and Trademarks*